United States Patent
Holtrup

(10) Patent No.: US 11,685,948 B2
(45) Date of Patent: Jun. 27, 2023

(54) METHOD FOR ANALYZING A NUCLEIC ACID SEQUENCE

(71) Applicant: SYSMEX CORPORATION, Kobe (JP)

(72) Inventor: Frank Holtrup, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 207 days.

(21) Appl. No.: 16/892,660

(22) Filed: Jun. 4, 2020

(65) Prior Publication Data

US 2020/0385783 A1    Dec. 10, 2020

(30) Foreign Application Priority Data

Jun. 4, 2019 (EP) .................... 19178104

(51) Int. Cl.
*C12Q 1/686* (2018.01)
*C12Q 1/6869* (2018.01)

(52) U.S. Cl.
CPC .......... *C12Q 1/686* (2013.01); *C12Q 1/6869* (2013.01)

(58) Field of Classification Search
CPC .... C12Q 1/686; C12Q 1/6869; C12Q 1/6848; C12Q 1/6806
See application file for complete search history.

(56) References Cited

U.S. PATENT DOCUMENTS

| 9,085,798 B2 | 7/2015 | Chee |
| 2014/0227705 A1* | 8/2014 | Vogelstein ........... C12Q 1/6806 435/6.12 |
| 2016/0362748 A1 | 12/2016 | Mongan et al. |

FOREIGN PATENT DOCUMENTS

| WO | 2016/010856 A1 | 1/2016 |
| WO | 2016/138080 A1 | 9/2016 |

OTHER PUBLICATIONS

Tian-Hao Zhang et al., "A benchmark study on error-correction by read-pairing and tag-clustering in amplicon-based deep sequencing", BMC Genomics, BioMed Central Ltd., London, UK, vol. 17, No. 1, Feb. 12, 2016, pp. 1-9, XP021233632; Cited in the extended European search report dated Dec. 13, 2019 in a counterpart European patent application.
Extended European search report dated Dec. 13, 2019 in a counterpart European patent application No. 19178104.6.

* cited by examiner

*Primary Examiner* — Cynthia B Wilder
(74) *Attorney, Agent, or Firm* — Sughrue Mion, PLLC

(57) ABSTRACT

Disclosed is a method for sequencing a nucleotide sequence of a target nucleic acid. The method comprises: providing a pool of amplicons, wherein the pool of amplicons is prepared by attaching a unique identifier to the target nucleic acid, and amplifying by PCR the target nucleic acid to which the unique identifier is attached; and sequencing the amplicons comprising the unique identifier and the target nucleic acid. In the method, a nucleotide sequence of the unique identifier comprises both a random nucleotide (N) and a predetermined nucleotide.

12 Claims, 16 Drawing Sheets

Specification includes a Sequence Listing.

UID: unique identifier
t-PS1: 1st target-specific primer section
t-PS2: 2nd target-specific primer section
u-PS2: 2nd universal primer section
u-PS1: 1st universal primer section sp1: 1st spacer section
sp2: 2nd spacer section
TS: tag section

```
Pattern Example 1:NNNNNNNNAAAAAAAANNNNNNNNTCTTAAAAGGTCTTTGATTTGCG (SEQ ID NO:1)
Pattern Example 2:NNNNNNNNAAAAAANNNNNNNTCTTAAAAGGTCTTTGATTTGCG (SEQ ID NO:2)
Pattern Example 3:NNNNNNNNAAAANNNNNNNTCTTAAAAGGTCTTTGATTTGCG (SEQ ID NO:3)
Pattern Example 4:NNNNNNNNANANANANANANANTCTTAAAAGGTCTTTGATTTGCG (SEQ ID NO:4)
Pattern Example 5:NNANNANNNANNANNANNANTCTTAAAAGGTCTTTGATTTGCG (SEQ ID NO:5)
Pattern Example 6:NNNNNNNNANANANANANANANGGGTCTTAAAAGGTCTTTGATTTGCG (SEQ ID NO:6)
```

Figure 4

AS1: 1st adaptor section
AS2: 2nd adaptor section

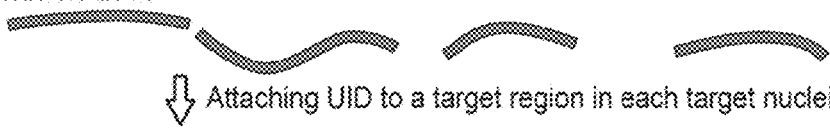
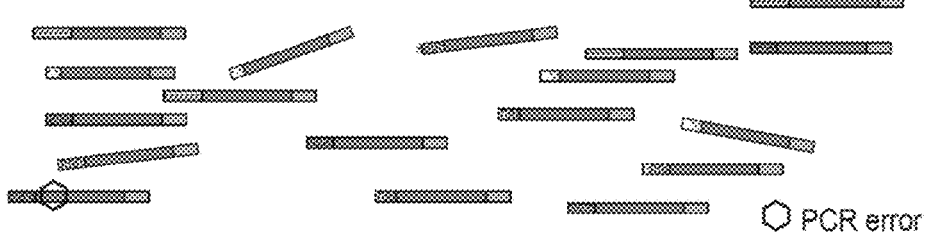
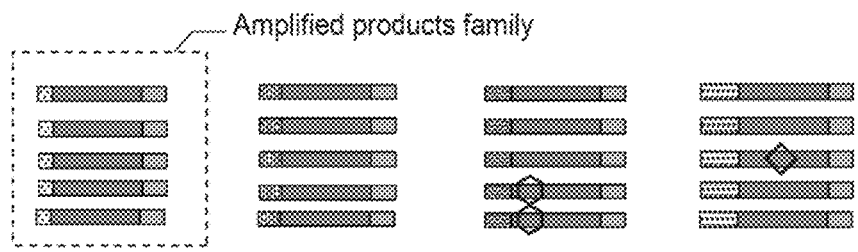
Figure 8

SEQUENCE LISTING

<160> NUMBER OF SEQ ID NOS: 25

<210> SEQ ID NO 1
<211> LENGTH: 44
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: n is a, c, g, t, or u
<220> FEATURE:
<221> NAME/KEY: misc_feature
<222> LOCATION: (15)..(21)
<223> OTHER INFORMATION: n is a, c, g, t, or u

<400> SEQUENCE: 1
nnnnnnnaaa aaaannnnnn ntcttaaaag gtctttgatt tgcg        44

<210> SEQ ID NO 2
<211> LENGTH: 42
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: n is a, c, g, t, or u
<220> FEATURE:
<221> NAME/KEY: misc_feature
<222> LOCATION: (13)..(19)
<223> OTHER INFORMATION: n is a, c, g, t, or u

<400> SEQUENCE: 2

```
nnnnnnnaaa aannnnnnnt cttaaaaggt ctttgatttg cg         42

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: n is a, c, g, t, or u
<220> FEATURE:
<221> NAME/KEY: misc_feature
<222> LOCATION: (11)..(17)
<223> OTHER INFORMATION: n is a, c, g, or t

<400> SEQUENCE: 3
nnnnnnnaaa nnnnnnntct taaaaggtct tgatttgcg              40

<210> SEQ ID NO 4
<211> LENGTH: 44
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: n is a, c, g, t, or u
<220> FEATURE:
<221> NAME/KEY: misc_feature
<222> LOCATION: (9)..(9)
<223> OTHER INFORMATION: n is a, c, g, t, or u
<220> FEATURE:
<221> NAME/KEY: misc_feature
<222> LOCATION: (11)..(11)
<223> OTHER INFORMATION: n is a, c, g, t, or u
<220> FEATURE:
<221> NAME/KEY: misc_feature
<222> LOCATION: (13)..(13)
<223> OTHER INFORMATION: n is a, c, g, t, or u
<220> FEATURE:
<221> NAME/KEY: misc_feature
<222> LOCATION: (15)..(15)
<223> OTHER INFORMATION: n is a, c, g, t, or u
<220> FEATURE:
<221> NAME/KEY: misc_feature
<222> LOCATION: (17)..(17)
<223> OTHER INFORMATION: n is a, c, g, t, or u
<220> FEATURE:
<221> NAME/KEY: misc_feature
<222> LOCATION: (19)..(19)
<223> OTHER INFORMATION: n is a, c, g, t, or u
<220> FEATURE:
<221> NAME/KEY: misc_feature
<222> LOCATION: (21)..(21)
<223> OTHER INFORMATION: n is a, c, g, t, or u

<400> SEQUENCE: 4
nnnnnnnana nanananana ntcttaaaag gtctttgatt tgcg        44

<210> SEQ ID NO 5
<211> LENGTH: 43
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(2)
<223> OTHER INFORMATION: n is a, c, g, t, or u
<220> FEATURE:
<221> NAME/KEY: misc_feature
```

```
<222> LOCATION: (4)..(5)
<223> OTHER INFORMATION: n is a, c, g, t, or u
<220> FEATURE:
<221> NAME/KEY: misc_feature
<222> LOCATION: (7)..(9)
<223> OTHER INFORMATION: n is a, c, g, t, or u
<220> FEATURE:
<221> NAME/KEY: misc_feature
<222> LOCATION: (11)..(12)
<223> OTHER INFORMATION: n is a, c, g, t, or u
<220> FEATURE:
<221> NAME/KEY: misc_feature
<222> LOCATION: (14)..(15)
<223> OTHER INFORMATION: n is a, c, g, t, or u
<220> FEATURE:
<221> NAME/KEY: misc_feature
<222> LOCATION: (17)..(18)
<223> OTHER INFORMATION: n is a, c, g, t, or u
<220> FEATURE:
<221> NAME/KEY: misc_feature
<222> LOCATION: (20)..(20)
<223> OTHER INFORMATION: n is a, c, g, t, or u

<400> SEQUENCE: 5
nnannannna nnannannan tcttaaaagg tctttgattt gcg                       43

<210> SEQ ID NO 6
<211> LENGTH: 47
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: n is a, c, g, t, or u
<220> FEATURE:
<221> NAME/KEY: misc_feature
<222> LOCATION: (9)..(9)
<223> OTHER INFORMATION: n is a, c, g, t, or u
<220> FEATURE:
<221> NAME/KEY: misc_feature
<222> LOCATION: (11)..(11)
<223> OTHER INFORMATION: n is a, c, g, t, or u
<220> FEATURE:
<221> NAME/KEY: misc_feature
<222> LOCATION: (13)..(13)
<223> OTHER INFORMATION: n is a, c, g, t, or u
<220> FEATURE:
<221> NAME/KEY: misc_feature
<222> LOCATION: (15)..(15)
<223> OTHER INFORMATION: n is a, c, g, t, or u
<220> FEATURE:
<221> NAME/KEY: misc_feature
<222> LOCATION: (17)..(17)
<223> OTHER INFORMATION: n is a, c, g, t, or u
<220> FEATURE:
<221> NAME/KEY: misc_feature
<222> LOCATION: (19)..(19)
<223> OTHER INFORMATION: n is a, c, g, t, or u
<220> FEATURE:
<221> NAME/KEY: misc_feature
<222> LOCATION: (21)..(21)
<223> OTHER INFORMATION: n is a, c, g, t, or u

<400> SEQUENCE: 6
nnnnnnnana nanananana ngggtcttaa aaggtctttg atttgcg                   47

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide primer
```

```
<400> SEQUENCE: 7
cctacacgac gctcttccga tct                                          23

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 8
tcttaaaagg tctttgattt gcg                                          23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 9
tcagacgtgt gctcttccga tct                                          23

<210> SEQ ID NO 10
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 10
tgcagtagcc gcctgc                                                  16

<210> SEQ ID NO 11
<211> LENGTH: 60
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(37)
<223> OTHER INFORMATION: n is a, c, g, or t

<400> SEQUENCE: 11
cctacacgac gctcttccga tctnnnnnnn nnnnnnntct taaaggtct ttgatttgcg    60

<210> SEQ ID NO 12
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 12
cctacacgac gctcttccga tctnnnnnnn ttttttnnn nnntcttaa aagtctttg      60 atttgcg                                                            67
```

```
<210> SEQ ID NO 13
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 13
cctacacgac gctcttccga tctnnnnnnn tntntntntn tntntcttaa aaggtctttg      60
atttgcg                                                               67

<210> SEQ ID NO 14
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
```

<223> OTHER INFORMATION: n is a, c, g, or t

<400> SEQUENCE: 14
cctacacgac gctcttccga tcttnntnnt nntnntnntn ntnntcttaa aaggtctttg    60
atttgcg                                                              67

<210> SEQ ID NO 15
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 15
cctacacgac gctcttccga tctnnnnnnn aaaaaaannn nnntcttaa aaggtctttg    60 atttgcg                                                              67

<210> SEQ ID NO 16
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 16
cctacacgac gctcttccga tctnnnnnnn ccccccennn nnntcttaa aaggtctttg    60 atttgcg                                                              67

<210> SEQ ID NO 17
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 17
cctacacgac gctcttccga tctnnnnnnn gggggggnnn nnntcttaa aaggtctttg    60 atttgcg                                                              67

<210> SEQ ID NO 18
<211> LENGTH: 67
<212> TYPE: DNA
<213> ORGANISM: Artificial Sequence

```
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 18
cctacacgac gctcttccga tctnnnnnnn atcgatcnnn nnnntcttaa aaggtctttg      60
atttgcg                                                               67

<210> SEQ ID NO 19
<211> LENGTH: 65
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (36)..(42)
<223> OTHER INFORMATION: n is a, c, g, or t

<400> SEQUENCE: 19
cctacacgac gctcttccga tctnnnnnnn tttttnnnnn nntcttaaaa ggtctttgat      60
ttgcg                                                                 65

<210> SEQ ID NO 20
<211> LENGTH: 63
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (34)..(40)
<223> OTHER INFORMATION: n is a, c, g, or t

<400> SEQUENCE: 20
cctacacgac gctcttccga tctnnnnnnn tttnnnnnnn tcttaaaagg tctttgattt      60
gcg                                                                   63

<210> SEQ ID NO 21
<211> LENGTH: 61
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (32)..(38)
<223> OTHER INFORMATION: n is a, c, g, or t

<400> SEQUENCE: 21
```
cctacacgac gctcttccga tctnnnnnnn tnnnnnnntc ttaaaaggtc tttgatttgc    60
g                                                                  61

<210> SEQ ID NO 22
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 22
cctacacgac gctcttccga tctnnnnnnn ananananan anantcttaa aaggtctttg    60
atttgcg                                                            67

<210> SEQ ID NO 23
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature

```
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 23
cctacacgac gctcttccga tctnnnnnnn cncncncncn cncntcttaa aaggtctttg    60
atttgcg                                                             67

<210> SEQ ID NO 24
<211> LENGTH: 67
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 24
cctacacgac gctcttccga tctnnnnnnn gngngngngn gngntcttaa aaggtctttg    60
atttgcg                                                             67

<210> SEQ ID NO 25
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 25
tcagacgtgt gctcttccga tcttgcagta gccgcctgc                          39
```

METHOD FOR ANALYZING A NUCLEIC ACID SEQUENCE

TECHNICAL FIELD

The present invention relates to a method for analyzing a nucleic acid sequence.

BACKGROUND

A technique is known which generates an amplicon with a primer containing a random sequence and analyzes the sequence of the amplicon.

For example, US 2015/0,361,492 A1 discloses Safe-Sequencing System, which uses a unique identifier (UID) sequence to identify mutations present in small DNA fragments by a sequencer.

US 2018/051,277 A1 describes a method for inserting a barcode sequence into a target nucleic acid using a "hairpin barcode primer" in a pre-amplification step of PCR.

The UID of US 2015/0,361,492 A1 and the barcode of US 2018/051,277 A1 are random sequences. The present inventors have found that nonspecific amplification products such as primer dimers are generated in PCR using a primer containing a random sequence as a tag. The nonspecific amplification product is also subject to sequence analysis, which can lead to inefficiencies in sequencing (off-target reads).

The hairpin barcode primer described in US 2018/051,277 A1 is a method of trying to prevent a binding of UID with other primers by allowing the primer to take a hairpin loop structure during the pre-amplification step, thus making the UID inaccessible to suppress a nonspecific amplification reaction. However, this method has a problem that the amplification conditions of the pre-amplification step are limited because it is necessary to maintain the hairpin loop structure in the pre-amplification step. In addition, it is necessary to use a base sequence that can maintain the hairpin structure, and there are major limitations in design of the sequence.

SUMMARY

An object of the present invention is to suppress generation of nonspecific amplification products in nucleic acid amplification using a primer containing a random sequence.

The present invention provides:
1. A method for sequencing a nucleotide sequence of a target nucleic acid, comprising:
   providing a pool of amplicons, wherein the pool of amplicons is prepared by attaching a unique identifier to the target nucleic acid, and amplifying by PCR the target nucleic acid to which the unique identifier is attached; and
   sequencing the amplicons comprising the unique identifier and the target nucleic acid,
   wherein a nucleotide sequence of the unique identifier comprises both a random nucleotide (N) and a predetermined nucleotide.
2. The method according to item 1, wherein a nucleotide at the 5' end of the unique identifier is random nucleotide (N), and a nucleotide at the 3' end of the unique identifier is random nucleotide (N).
3. The method according to item 1 or 2, wherein the unique identifier comprises a plurality of predetermined nucleotides.
4. The method according to any one of items 1 to 3, wherein the unique identifier consists of one or more random nucleotides and one or more predetermined nucleotides.
5. The method according to any one of items 1 to 3, wherein the unique identifier consists of a random nucleotide (N) and a predetermined nucleotide (A), the predetermined nucleotide (A) comprises adenine as a base.
6. The method according to any one of items 1 to 3, wherein the unique identifier consists of a random nucleotide (N) and a predetermined nucleotide (G), the predetermined nucleotide (C) comprises guanine as a base.
7. The method according to any one of items 1 to 3, wherein the unique identifier consists of a random nucleotide (N) and a predetermined nucleotide (T), the predetermined nucleotide (T) comprises thymine as a base.
8. The method according to any one of items 1 to 3, wherein the unique identifier is consists of a random nucleotide (N) and a predetermined nucleotide (C) comprises cytosine as a base.
9. The method according to any one of items 1 to 8, wherein 6% to 90% of nucleotides of the unique identifier are predetermined nucleotides.
10. The method according to any one of items 1 to 9, wherein the nucleotide number of the unique identifier is Z nt, and the unique identifier comprises 1 nt to Z/2 nt of predetermined nucleotides.
11. The method according to claims any one of items 1 to 10, wherein the length of the unique identifier is 4 nt or more.
12. The method according to any one of items 1 to 11, wherein the length of the unique identifier is 100 nt or less.
13. The method according to any one of items 1 to 5, and 7 to 12, wherein the predetermined nucleotide does not comprise G.
14. A primer for attaching a unique identifier to a target nucleic acid to sequence the target nucleic acid, the primer comprising a unique identifier
   wherein a nucleotide sequence of the unique identifier comprises both a random nucleotide (N) and a predetermined nucleotide.
15. A use of a primer for the method according to item 1, the primer comprising a unique identifier
   wherein a nucleotide sequence of the unique identifier comprises both a random nucleotide (N) and a predetermined nucleotide.

BRIEF DESCRIPTION OF THE DRAWINGS

FIG. 4 shows examples of sequences of primers containing UID.

FIG. 5A shows an example of annealing of an antisense strand of the target nucleic acid and the primer containing UID. FIG. 5B shows an example of annealing of the reverse primer with a sense strand of the target nucleic acid.

FIG. 6A is an example of a tagged target nucleic acid produced when using a primer containing UID without containing a universal primer. FIG. 6B is an example of a tagged target nucleic acid prepared when using a universal primer and a primer containing UID.

FIG. 7A is an example of a primer containing an adaptor section, a universal primer section, and UID. FIG. 7B is an example of a reverse primer containing an adaptor section, a universal primer section, and UID. FIG. 7C is an example of a tagged target nucleic acid containing an adaptor prepared when using the universal primer with an adaptor section and the primer containing UID.

FIG. 8 shows features of Plasma-Safe-Sequencing technology.

FIG. 9A is an example in which a target nucleic acid sequencing apparatus and an analysis apparatus are configured independently. FIG. 9B is an example in which a target nucleic acid sequencing apparatus and an analysis apparatus are integrated.

DETAILED DESCRIPTION OF THE PREFERRED EMBODIMENTS

Abbreviations used in the present specification and drawings have the following meanings.
UID: unique identifier
TN: Target nucleic acid
TS: Tag section
u-PS1: 1st Universal primer section
t-PS1: 1st Target-specific primer section
u-PS2: 2nd Universal primer section
t-PS2: 2nd Target-specific primer section
AS1: 1st Adaptor section
AS2: 2nd Adaptor section
sp1: 1st Spacer section
sp2: 2nd Spacer section
c-TS: Complementary strand of tag section
c-u-PS1: Complementary strand of 1st universal primer section (complementary strand of 1st universal primer section)
c-t-PS1: Complementary strand of 1st target-specific primer section (complementary strand of 1st target-specific primer section)
c-u-PS2: Complementary strand of 2nd universal primer section (complementary strand of 2nd universal primer section)
c-t-PS2: Complementary strand of 2nd target-specific primer section (complementary strand of 2nd target-specific primer section)
c-AS1: Complementary strand of 1st adaptor section (complementary strand of 1st adaptor section)
c-AS2: Complementary strand of 2nd adaptor section (complementary strand of 2nd adaptor section)
T: Nucleotide in which base moiety is thymine and sugar moiety is deoxyribose
U: Nucleotide in which base moiety is uracil and sugar moiety is deoxyribose
A: Nucleotide in which base moiety is adenine and sugar moiety is deoxyribose
G: Nucleotide in which base moiety is guanine and sugar moiety is deoxyribose
C: Nucleotide in which base moiety is cytosine and sugar moiety is deoxyribose
N: Random nucleotide
Abbreviations for nucleotides follow the IUPAC nucleotide code.

The unit "nt" means a length of sequence, i.e., the number of nucleotides, in the following description.

Figure 1A:
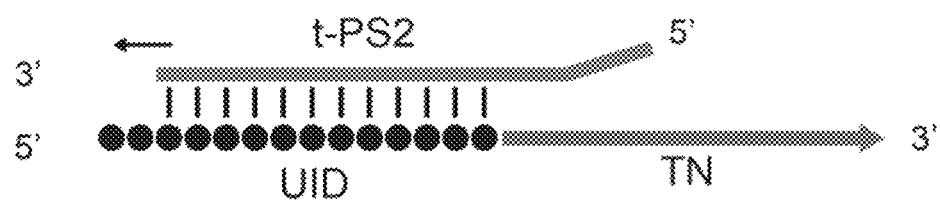
FIG. 1A is a schematic diagram showing that a reverse primer nonspecifically bound to a forward primer containing a random sequence thus amplifying off-target product.

The UID is a partial region of the primer oligonucleotide and is composed of a plurality of random nucleotides. In the art, random sequences in the primer oligonucleotides are referred to as unique identifiers, barcodes, random barcodes, molecular barcodes, or the like, and they all have the same meaning herein.

u-PS1, UID (black circles indicate any random nucleotide selected from A, T, G and C) used in the conventional method (hereinafter, nucleotides in the random sequence are represented by "N"), and there was a problem that a tagged primer containing t-PS1 nonspecifically binds to a reverse primer containing u-PS2 and t-PS2 during amplification by PCR to generate a nonspecific amplification product such as a primer dimer. FIG. 1A is a schematic diagram showing that a reverse primer was nonspecifically bound to a forward primer containing a random sequence. Here, forward primers containing random sequences may cause nonspecific binding.

Figure 1B:
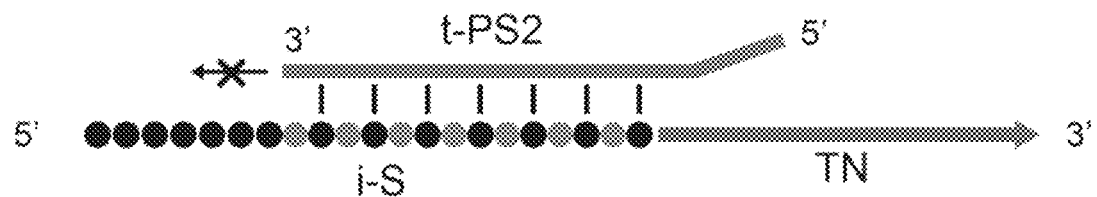
FIG. 1B is a diagram showing a problem solving means of the present disclosure. The black dot indicates a random nucleotide and the gray dot indicates a predetermined nucleotide.

The present disclosure, as shown in FIG. 1B, suppresses nonspecific amplification reactions of the tagged primer and the reverse primer, by inserting a predetermined nucleotide (represented by gray circles. Gray circles indicate any predetermined nucleotide selected from A, T, G and C) in the UID sequence, or by replacing a part of the UID sequence with a predetermined nucleotide. That is, in the UID in the tagged primer, N and A, T, G or C are mixed. Because a sequence of random sequence cannot be determined in advance, it is not possible to suppress nonspecific binding to other DNA molecules. However, it is considered that the number of nonspecifically formed hydrogen bonds can be reduced as compared to that in the UID consisting of only random sequences, by containing a predetermined nucleotide in the random sequence (refer to FIG. 1B).

1. Method for Determining Target Nucleic Acid Sequence

A method for determining a target nucleic acid sequence determines a nucleic acid sequence of a target nucleic acid. The method for determining a target nucleic acid sequence can be applied to sequencing using a tag sequence added with UID or containing UID.

A method for determining a target nucleic acid sequence includes a step A of preparing a library of amplicons (hereinafter simply referred to as "pool of amplicons") containing UID produced using a polynucleotide containing a target nucleic acid as a template nucleic acid, and a step B of sequencing the amplicons. The method may include a step C of determining an accurate sequence of a target region using sequence information having the same UID sequence as an optional step.

The method for determining a target nucleic acid sequence may further include a step of outputting sequence information of the target nucleic acid.

Each step will be described in detail below.

[1-1. Step A: Preparation of Pool of Amplicons]

A target nucleic acid includes a full length or fragment of DNA (derived from genomic DNA, mitochondrial DNA, plasmid DNA, transposon DNA, etc.) to be analyzed, and a full length or fragment of RNA (derived from messenger RNA, ribosomal RNA, transfer RNA, microRNA, non-coding RNA, etc.) to be analyzed. The target nucleic acid may be represented by, for example, a gene name, and may be represented by GENE ID, Accession No., Reference Sequence ID, Chromosome Locus No., Reference SNP (refSNP) Cluster Report ID or the like described in The National Center for Biotechnology Information, or the like. The target nucleic acid is comprised in a nucleic acid sample. The nucleic acid sample can be a sample derived from a living body. Examples of the nucleic acid sample may include blood, serum, plasma, lymph fluid, ascetic fluid, bone marrow aspirate, nipple discharge, liquid prepared from tumor cell, saliva, and the like.

Preparation of the pool of amplicons is preferably done by PCR. The pool of amplicons can be prepared, for example, (1) by amplifying target nucleic acid by PCR using primers containing UID (UID addition and amplification steps). In another embodiment, the pool of amplicons can be prepared (2) by amplifying target nucleic acid in a first PCR using a tagged primer having a universal primer section and a tag section containing UID (tagged step), and amplifying the tagged target nucleic acid in a second PCR using a universal primer (amplification step). In one embodiment, the preparation of the pool of amplicons is conducted by mixing: a sample comprising the target nucleic acid derived from a living body; a reagent comprising the tagged primer that comprises the UID; and necessary materials for PCR such as a polymerase and dNTPs. The amplicon comprising the nucleotide sequence of the target nucleic acid and the UID is produced.

In the above case (1), at least a primer containing at least a UID is used as a primer. The number of PCR cycles is not particularly limited, and is preferably 10 to 50 cycles, and more preferably 20 to 40 cycles. Prior to the PCR, pre-amplification of the target nucleic acid may be performed using primers not containing UID. The primer not containing UID may be a primer specific to a target region or may be a random primer.

In the above case (2), at least two PCR reactions are performed. By the first PCR, it is possible to generate a DNA added with UID in a target region. After completion of the first PCR, the second PCR can be performed by mixing at least a part of the reaction product, a universal primer, and a polymerase. The number of first PCR cycles and the number of second PCR cycles are not particularly limited. The number of first PCR cycles is preferably 5 to 20 cycles, and more preferably 10 to 15 cycles. The number of second PCR cycles is preferably 10 to 30 cycles, and more preferably 15 to 25 cycles. Prior to the first PCR, pre-amplification may be performed using primers not containing a tag section. The primer not containing a tag section may be a primer specific to a target region or may be a random primer.

Hereinafter, with reference to FIG. 2 to FIG. 7, examples of preparation of a pool of amplicons using a primer containing UID or a tagged primer having a universal primer section and a tag section containing UID and the like will be specifically described.

Figure 2:
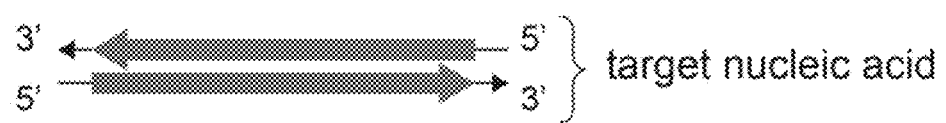
FIG. 2 is a diagram showing an example of a target nucleic acid.

A target nucleic acid shown in FIG. 2 is a double-stranded polynucleotide composed of a polynucleotide containing a target region and a complementary polynucleotide. The target nucleic acid may be single stranded.

Example of the target nucleic acid is a DNA extracted from a sample to be analyzed, a DNA library, cDNA obtained by reverse transcription of RNA extracted from the sample to be analyzed, and concentrated and purified DNA thereof. The extraction and concentration of DNA can be performed by a product commercially available.

The UID is contained in a forward primer and/or a reverse primer. FIG. 3 shows examples of forward primers containing UID and reverse primers not containing UID.

Figure 3A:
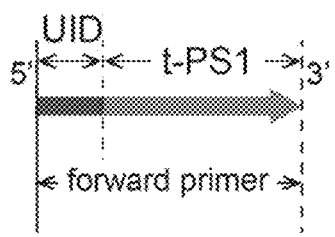
FIG. 3A is a diagram showing an example of a configuration of a forward primer for preparing a target nucleic acid bound to UID.
Figure 3B:
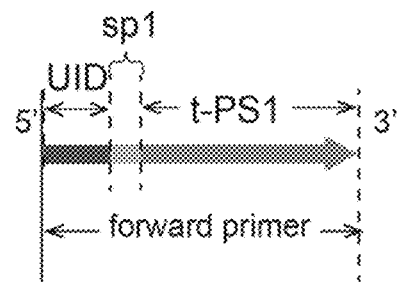
FIG. 3B is a diagram showing an example of a configuration of a primer containing a spacer for preparing a target nucleic acid bound to UID.
Figure 3C:
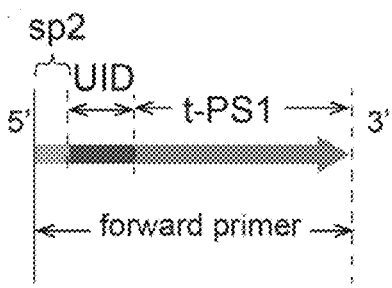
FIG. 3C is a diagram showing an example of a configuration of a forward primer containing a spacer for preparing a target nucleic acid bound to UID.
Figure 3D:
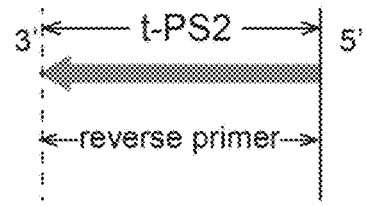
FIG. 3D is a diagram showing an example of a configuration of a reverse primer.

Examples of the forward primers and the reverse primer used in an embodiment of the above case (1) are shown in FIG. 3A to FIG. 3D. The primer shown in FIG. 3A is an example of a configuration of a forward primer for preparing a target nucleic acid bound to UID. In this example, the UID is contained on 5' side, and the 1st target-specific primer section (t-PS1) is contained on 3' side. t-PS1 functions as a primer that specifically amplifies a target nucleic acid. FIG. 3B is an example of a configuration of a primer containing a spacer for preparing a target nucleic acid bound to UID. In this example, the UID is contained on 5' side, t-PS1 is contained on 3' side, and a 1st spacer (sp-1) is contained between the UID and t-PS1. FIG. 3C is an example of a configuration of a forward primer containing a spacer for preparing a target nucleic acid bound to UID. In this example, a 2nd spacer (sp-2) is contained on 5' side, t-PS1 is contained on 3' side, and UID is contained between sp-2 and t-PS1. FIG. 3D is a diagram showing an example of a configuration of a reverse primer that does not contain UID.

Figure 3E:
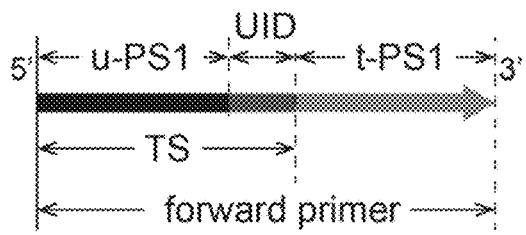
FIG. 3E is a diagram showing an example of a configuration of a forward primer for preparing a target nucleic acid bound to UID. The present example has a universal primer section at 5' terminal side of the primer.
Figure 3F:
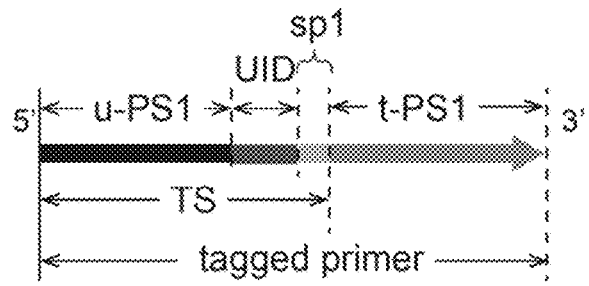
FIG. 3F is a diagram showing an example of a configuration of a forward primer containing the spacer for preparing a target nucleic acid bound to UID. The present example has a universal primer section at 5' terminal side of the primer.
Figure 3G:
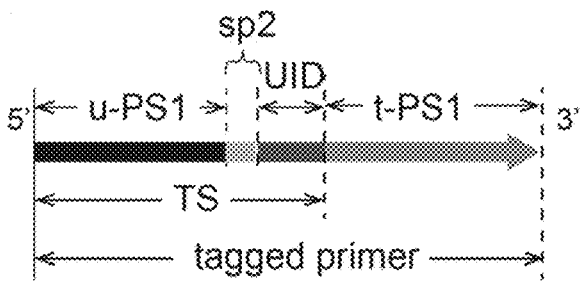
FIG. 3G is a diagram showing an example of a configuration of a forward primer containing the spacer for preparing a target nucleic acid bound to UID. The present example has a universal primer section at 5' terminal side of the primer.
Figure 3H:
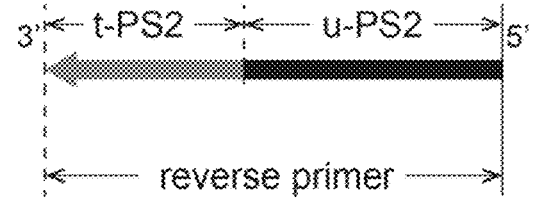
FIG. 3H is a diagram showing an example of a configuration of a reverse primer. The present example has a universal primer section at 5' terminal side of the primer.

Examples of the forward primers and the reverse primer used in an embodiment of the above case (2) are shown in FIG. 3E to FIG. 3H. In the present embodiment, the primer may contain a universal primer section. FIG. 3E is a diagram showing an example of a configuration of a forward primer for preparing a target nucleic acid bound to UID. The present example contains a 1st universal primer section (u-PS1) at 5' terminal side of the primer, contains t-PS1 at 3' side, and contains UID between u-PS1 and t-PS1. FIG. 3F is a diagram showing an example of a configuration of a forward primer containing a spacer for preparing a target nucleic acid bound to UID. In this example, the present example contains u-PS1, UID, sp1 and t-PS1 from 5' terminal side of the primer. FIG. 3G is a diagram showing an example of a configuration of a forward primer containing a spacer for preparing a target nucleic acid bound to UID. The present example contains u-PS1, sp2, UID and t-PS1 from 5' terminal side of the primer. FIG. 3H is a diagram showing an example of a configuration of a reverse primer. The present example has a 2nd universal primer section (u-PS2) at 5' terminal side of the primer. A portion containing u-PS1 and UID, a portion of u-PS1, UID and sp1, and a portion of u-PS1, sp2 and UID are also referred to as tag sections.

The length of the UID sequence can be determined according to the number of target nucleic acid molecules in a sample. When the number of target nucleic acid molecules is small, the number of random nucleotides in the UID may be small. Usually, the length of UID (the total number of random nucleotides and the predetermined number of nucleotides) is 3 nucleotides or more, and preferably 5 nucleotides or more. The upper limit of the length of UID is not particularly limited, and is usually 120 nt or less, and preferably 100 nt or less, in consideration of amplification efficiency and read length analyzed by a sequencer.

The UID contains a plurality of random nucleotides (N) and predetermined nucleotides (A, T/U, G or C). That is, random nucleotides and predetermined nucleotides are mixed in the UID. When the UID is all composed of random nucleotides, the sequence cannot be predicted, which may result in a sequence nonspecifically bound to other primer molecules and the like. However, nonspecific binding to other primer molecules and the like can be suppressed by inserting a predetermined nucleotide which is less likely to cause nonspecificity in advance. For example, when the UID of a certain primer molecule contains "A" as the predetermined nucleotide at 5th from 5' end as the predetermined nucleotide, the same position is A also for other primer molecules. Therefore, these primer molecules are less susceptible to nonspecific binding at least at the 5th from the 5' end.

The UID is attached to each molecule of the target nucleic acid contained in the sample. In this case, it is possible to identify from which molecule in the sample the sequence of the amplicon is derived. In this case, the random sequence may be preferably a unique identifier (UID) as described in US 2015/0,361,492 A1. US 2015/0,361,492 A1 is incorporated herein by reference.

The type of predetermined nucleotide is determined in advance during primer synthesis. In preparing the pool of amplicons, a sufficient amount of primers for synthesis is added to a reaction system. Although N in the nucleotide sequence of UID differs for each primer molecule, the predetermined nucleotides are designed to be identical among the primer molecules. For example, when the UID is attached to the forward primer, in a case where 1st to 4th and 6th to 10th positions from the 5' end are random sequences and 5th is "A", 5th nucleotides of all forward primer molecules are "A".

The positions of the random nucleotide and the predetermined nucleotide at the UID are not particularly limited as long as they can suppress generation of nonspecific amplification products during PCR. Both the 5' end and 3' end of the UID are random nucleotides. Provided that the number of nucleotides in UID is Z nt, the number of predetermined nucleotides can be appropriately selected from 1 nt or more, 2 nt or more, 3 nt or more, 4 nt or more, 5 nt or more, 6 nt or more, 7 nt or more, 8 nt or more, 9 nt or more, 10 nt or more, 11 nt or more, 12 nt or more, 13 nt or more, 14 nt or more, 15 nt or more, 16 nt or more, 17 nt or more, 18 nt or more, 19 nt or more, 20 nt or more, 21 nt or more, 22 nt or more, 23 nt or more, 24 nt or more, and 25 nt or more, in a range not exceeding (Z/2) nt. Preferably it is 3 nt or more. These numerical values may be appropriately combined to configure a certain range. For example, the range of the number of predetermined nucleotides can be 1 nt to 25 nt, and preferably 3 nt to 25 nt.

In another embodiment, when the nucleotide number X nt of UID is 100%, the proportion of predetermined nucleotides in UID can be properly selected from 6% or more, about 6.6 ($1/15$)% or more, about 7.1 ($1/14$)% or more, about 13.7 ($2/15$)% or more, about 17.6 ($3/17$)% or more, about 22.2 ($4/18$)% or more, about 26.3 ($5/19$)% or more, 30 ($6/20$)% or more, about 33.3 ($7/21$)% or more, about 36.4 ($8/22$)% or more, about 39.1 ($9/23$)% or more, about 41.7 ($10/24$)% or more, 44 ($11/25$)% or more, about 46.2 ($12/26$)% or more, about 48.1 ($13/27$)% or more, and 50 ($14/28$)% These numerical values may be appropriately combined to configure a certain range. For example, the range of the proportion of predetermined nucleotides can be 6% to 90%, preferably 6% to 50%, and more preferably about 17.6 ($3/17$)% to 50%.

When the UID contains 2 nt or more predetermined nucleotides, the predetermined nucleotides may be present continuously or discontinuously in the UID.

The predetermined nucleotide is not limited as long as it is a nucleotide selected from T or U, A, G, and C. It is preferably a nucleotide selected from T, A and C, and more preferably a nucleotide selected from T and A. The binding of T to A is weaker than the binding of G to C, and thus is preferable from the viewpoint of nonspecific binding inhibition.

When the UID contains a plurality of predetermined nucleotides, in a preferred embodiment, the predetermined nucleotide A and the predetermined nucleotide T are not mixed. In another preferred embodiment, the predetermined nucleotide G and the predetermined nucleotide C are not mixed. In a more preferred embodiment, the predetermined nucleotides in the UID are all A. In another more preferred embodiment, the predetermined nucleotides in the UID are all T. In another more preferred embodiment, the predetermined nucleotides in the UID are all C. In another more preferred embodiment, the predetermined nucleotides in the UID are all G. This configuration can further suppress the binding between the primers.

The forward primers shown in FIG. 3B, FIG. 3C, FIG. 3F, and FIG. 3G contains a 1st spacer section (sp1) or a 2nd spacer section (sp2). The spacer section may contain one or more nucleotides selected from T, U, A, C and G. Preferably, the spacer section may be 2 nt, 3 nt, 4 nt or 5 nt. When the number of nucleotides contained in the spacer section is 2 nt or more, each nucleotide may be the same or different. sp1 and sp2 may be continuous to the 5' end and 3' end of the UID, respectively.

FIG. 4 shows examples of sequences of UIDs. In FIG. 4, "N" indicates a random nucleotide. FIG. 4 exemplifies a case where the predetermined nucleotide "X" is "A". "CCTACACGACGCTCTTCCGATCT (SEQ ID NO: 7)" indicates u-PS1, and "TCTTAAAAGGTCTTTGATTTGCG (SEQ ID NO: 8)" indicates t-PS1. A tagged primer set forth in SEQ ID NO: 1 is an example containing 7 nt predetermined nucleotides in the middle of a 14 nt random sequence. A tagged primer set forth in SEQ ID NO: 2 is an example containing 5 nt predetermined nucleotides in the middle of a 14 nt random sequence. A tagged primer set forth in SEQ ID NO: 3 is an example containing 3 nt predetermined nucleotides in the middle of a 14 nt random sequence. A tagged primer set forth in SEQ ID NO: 4 is an example in which 7 nt random nucleotides and 7 nt predetermined nucleotides alternate in 7 nt on the latter side of a 14 nt random sequence. A tagged primer set forth in SEQ ID NO: 5 is an example in which 1 nt predetermined nucleotides are present at every 2 nt or 3 nt of 14 nt random nucleotides. A tagged primer set forth in SEQ ID NO: 6 is an example in which sp1 (herein exemplified by underlined GGG) is present between UID and t-PS1 in the tagged primer set forth in SEQ ID NO: 5.

The reverse primer shown in FIG. 3D contains a 2nd target-specific primer section (t-PS2). The reverse primer may contain a 2nd universal primer section (u-PS2) and the like on the 5' side of t-PS2. The reverse primer is an example containing u-PS2 and t-PS2 in order from the 5' side. t-PS2 has a sequence complementary to a part of the sequence on the 3' side of the target sequence.

The universal primer section may be a section containing the same sequence as the universal primer used for sequencing. Herein, the "universal primer" is a primer capable of amplifying an amplicon, regardless of the UID sequence and the sequence of the target nucleic acid. As a sequence of the universal primer section, a known sequence can be used, and example thereof includes a sequence derived from M13 phage, the iX and iY sequences provided by Illumina, Inc. The UID is a section containing a sequence for identifying each amplicon, and preferably a sequence not present in the target region or the universal primer section.

The length of the universal primer section sequence is not particularly limited, and it is about 5 to 25 nt.

The length of the target-specific primer section sequence is not limited as long as it can be annealed with a template nucleic acid. For example, the length of the target-specific primer section sequence is about 5 to 50 nt, and preferably about 10 to 30 nt. The length of the target-specific primer section sequence is expressed as "m" in some cases. m is a positive integer. The target-specific primer section sequence need not be perfectly complementary to the target sequence as long as it hybridizes to the target nucleic acid and functions as a primer. For example, the target-specific primer section sequence may not be complementary to the target sequence, by about 1 nt, 2 nt, or 3 nt.

Figure 5A:
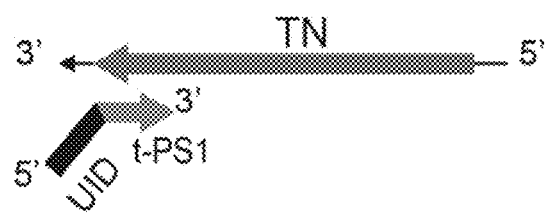
FIGS. 5A-5B show diagrams of examples of annealing of a target nucleic acid with a primer containing UID and a reverse primer.
Figure 5B:
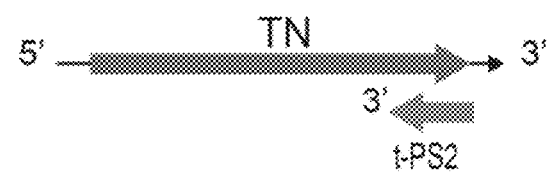

FIG. 5 shows diagrams of examples of annealing of a target nucleic acid with a forward primer containing UID and a reverse primer. FIG. 5A is an example in which a primer containing UID that functions as a forward primer hybridizes to TN. FIG. 5B is an example in which a reverse primer hybridizes to TN. After annealing, an elongation reaction can be carried out using DNA polymerase according to a known method.

Figure 6A:
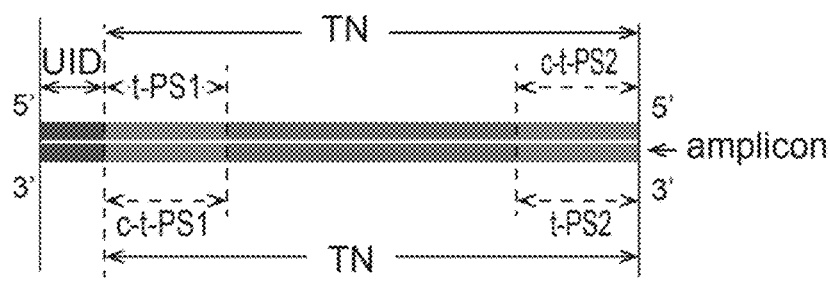
FIGS. 6A-6B show examples of structures of tagged target nucleic acids.
Figure 6B:
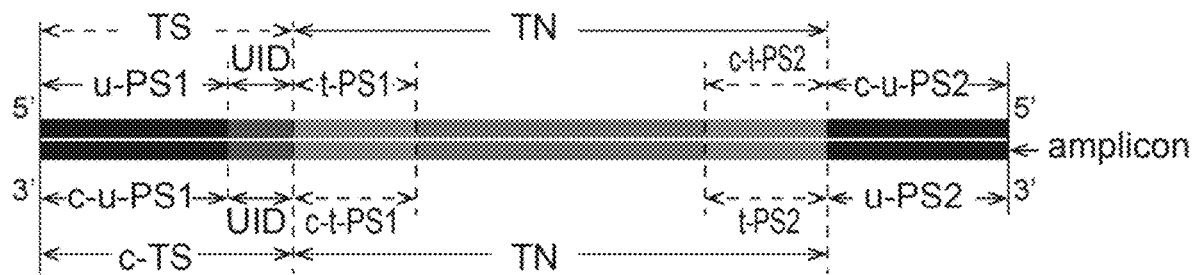

An example of the structure of the tagged target nucleic acid produced by the elongation reaction is shown in FIG. 6. FIG. 6A is an example of a target nucleic acid added with UID, which is produced by the forward primer shown in FIG. 3A and the reverse primer shown in FIG. 3D. FIG. 6B is an example of a tagged target nucleic acid added with UID, which is produced by the forward primer shown in FIG. 3E and the reverse primer shown in FIG. 3H. A pool of amplicons is prepared by amplifying the target nucleic acid or tagged target nucleic acid added with UID, for example, by a PCR method. Generally, an amplicon is in a double-stranded state in which it is bound to a complementary strand.

In this example, the amplicons are lower strands shown in FIG. 6A and FIG. 6B. The amplicon contains c-u-PS1, UID, TN and u-PS2 from 3' side. c-t-PS1 and t-PS2 are located in TN. The amplicon complementary strand contains u-PS1, UID, TN, and c-u-PS2 from 5' side. t-PS1 and c-t-PS2 are located in TN.

Figures 7A, 7B:
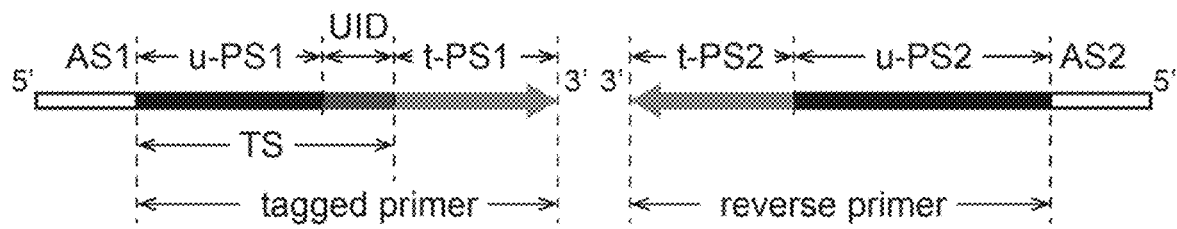
FIGS. 7A-7C show diagrams of other examples of primers containing UID and a reverse primer.

Other examples of the tagged primer and the reverse primer are shown in FIG. 7A and FIG. 7B. This tagged primer shown in FIG. 7A contains a 1st adaptor section (AS1) at 5' terminal side. The tagged primer can be used to immobilize the amplicon to a solid phase. The reverse primer shown in FIG. 7B contains a 2nd adaptor section (AS2) on 5' side. These adaptor sections are used when sequencing of amplicons is performed on a solid phase (flow cell, bead, etc.). For example, a sequence complementary to the adaptor section can be immobilized on the solid phase in advance. An amplicon prepared using a primer containing an adaptor section has adaptor sections at both ends thereof, so that the amplicon can be immobilized on the solid phase. Amplicon synthesis using a primer containing an adaptor section is the same as FIG. 2 to FIG. 6, except that the adaptor sections are added to the terminals.

Figure 7C:
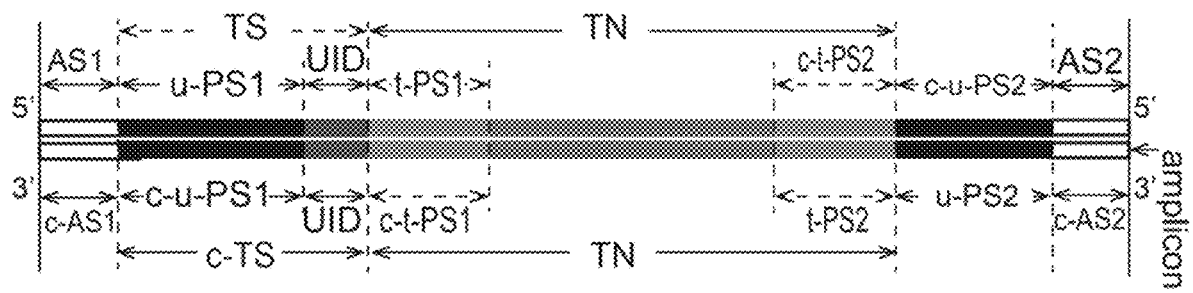

An example of the structure of the tagged target nucleic acid produced by the elongation reaction is shown in FIG. 7C. FIG. 7C is an example of a target nucleic acid added with UID, which is produced by the forward primer shown in FIG. 7A and the reverse primer shown in FIG. 7B. A pool of amplicons is prepared by amplifying the tagged target nucleic acid, for example, by PCR method. Generally, an amplicon is in a double-stranded state in which it is bound to a complementary strand.

In this example, the amplicon is a lower strand shown in FIG. 7C. The amplicon contains c-AS1, c-u-PS1, UID, TN, u-PS2 and c-AS2 from 3' side. c-t-PS1 and t-PS2 are located in TN. The amplicon complementary strand contains AS1, u-PS1, UID, TN, c-u-PS2 and AS2 from 5' side. t-PS1 and c-t-PS2 are located in TN.

[1-2. Step B: Sequencing]

In step B, the amplicon is sequenced. Sequence information (read) of the target region is obtained by this sequencing. The sequence information is information obtained by converting detected fluorescence signals, ions or the like as information indicating each nucleotide in a sequencer into nucleotide information of A, G, T and C, respectively, and arranging them in order of detection (ascending order). Normally, the sequence information is obtained from the 5' side. A sequencer (automatic sequence analyzer) is usually used for sequencing. The sequencer is not limited as long as sequence information can be obtained from the amplicon, and a known device can be used. The sequencer is preferably a next generation sequencer. Examples of the next generation sequencer include MiSeq (registered trademark), HiSeq (registered trademark), NextSeq (registered trademark), MiniSeq (registered trademark), NovaSeq (registered trademark) of Illumina Inc. (San Diego, Calif.); Ion Proton (registered trademark), Ion PGM (registered trademark) of Thermo Fisher Scientific, Inc. (Waltham, Mass.); GS FLX+ (registered trademark) and GS Junior (registered trademark) of F. Hoffmann-La Roche, Ltd. (Basel, Switzerland); and the like.

For example, a sequencer of Illumina Inc. can amplify polynucleotides of enormous numbers of target regions on a flow cell by combining Bridge PCR method and Sequencing-by-synthesis method and perform sequencing of the amplification product.

A universal primer that binds c-u-PS1 can be used as a sequencing primer. According to this, it is possible to obtain information of sequences containing UID and TR. Also, information of sequences containing c-TR and complementary sequence of UID can also be obtained using a universal primer that binds to c-u-PS2.

[1-3. Step C: Determination of Sequence of Target Region]

A step C of determining an accurate sequence of the target region using the sequence information obtained in step B may be further performed.

Changes (errors) in nucleotide sequence caused by in vitro manipulations such as PCR and sequencing are generally referred to as PCR errors or sequencing errors, and are sequences not present in the sequence of the target nucleic acid as a template.

In this step, it is determined whether the sequence information obtained in step B reflects the sequence of the target nucleic acid, that is, whether or not the sequence of the target region is an accurate sequence.

Whether or not the sequence of the target region is an accurate sequence can be discriminated by, for example, the technique of US 2015/0361492 A1.

Specifically, the origin of each amplicon can be identified by the UID sequence contained in the sequence information as described in the above 1-1. As exemplified in FIG. 8, when the above-described UID is used as a random sequence, daughter molecules with different UID sequences for each target nucleic acid are prepared from the target region of multiple copies of target nucleic acids (in this example, there is one type of target region contained in the target nucleic acid) present in a DNA sample (FIG. 8: Step A1). Next, the daughter molecules to which the UID sequence is added are amplified by PCR using a universal primer to prepare a pool of amplicons (FIG. 8: Step A2). The pool of amplicons prepared as above contains amplicons amplified using each daughter molecule to which the UID sequence is added as a template. Step A shown in FIG. 8 corresponds to step A described in the above 1-1.

Next, sequencing of each amplicon is performed. Step B shown in FIG. 8 corresponds to step B described in the above 1-2.

Next, in step C of FIG. 8, an accurate sequence of the target region is determined. Specifically, sequence information having the same UID sequence is determined in step C1 of FIG. 8. The sequence information of all daughter molecules amplified from one template molecule has all the same UID sequence. A group of amplicons having the same UID sequence is referred to as "family", and an individual amplicon having the same UID family is referred to as "member". Whether or not they have the same UID sequence can be determined by comparing the sequence information with a predetermined length at the 5' terminal side of the sequence information.

Next, in step C2 of FIG. 8, whether or not the sequence of the target region is an accurate sequence is determined using the family sequence information.

In step C2 of FIG. 8, first, comparison (alignment) of sequence information is made within this same family. By this alignment, a nucleotide showing a consensus rate of not less than a predetermined value in each position in the sequence information is determined as a nucleotide of the target region. This determination is performed at all positions of the sequence information, and an accurate sequence of entire sequence of the target region is determined. By doing this, PCR errors, sequencing errors and the like are eliminated. It is because PCR errors, sequencing errors and the like are generally 0 to several % within the family, and hardly become majority within the family.

The predetermined value may be 1%, 5%, 10%, 20%, 30%, 40%, 50%, 60%, 70%, 80%, or 90%. The predetermined value is preferably 80% or 90%.

[1-4. Mutation Detection Method]

The method for determining a target nucleic acid sequence may include a mutation detection step D in addition to the above steps A to C. In the present specification, the term "mutation" means that a specific base in the wild-type sequence is replaced, deleted or inserted with another base in vivo.

In step D, a reference sequence and the sequence information of each family analyzed in step C are compared. The reference sequence may be a wild-type sequence of the target region. When a nucleotide different from the reference sequence is present in the sequence of a part of family, this sequence can be determined to be derived from mutant DNA in a sample. In this case, it can be determined that the sample DNA contains a mutation. In the absence of a nucleotide different from the reference sequence, it can be determined that the sample DNA does not contain a mutation.

As the reference sequence, a sequence registered in the public sequence information database can be used. As the public sequence information database, NCBI RefSeq (web page, www.ncbi.nlm.nih.gov/refseq/), NCBI GenBank (web page, www.ncbi.nlm.nih.gov/genbank/), UCSC Genome Browser, and the like, may be used. As the reference sequence, a sequence registered in a publicly known mutation information database may be used. Examples of publicly known mutation information databases include COSMIC database (web page, www.sanger.ac.uk/genetics/CGP/cosmic/), ClinVar database (web page, www.ncbi.nlm.nih.gov/clinvar/), dbSNP (web page, www.ncbi.nlm.nih.gov/SNP/), HapMap Genome Browser release #28, Human Genetic Variation Browser (web page, www.genome.med.kyoto-u.ac.jp/SnpDB/index.html), and 1000 Genomes (web page, www.1000genomes.org/).

Further, the result of sequence analysis may be outputted. The output method is not particularly limited, and, for example, the analysis result may be displayed on a monitor of a sequencing apparatus, transmitted to another terminal, or printed out on paper. When a mutation detection result is outputted, the presence or absence of a mutation may be outputted. When there is a mutation, an explanation of the analysis result on the mutation (type of mutation, site of mutation, etc.) may be added.

In another embodiment, in addition to steps A and B above, steps C' and D' are included. Step C' includes steps C1 and C2'. Step C1 is as described in the above 1-3. In step C2', each sequence information of the amplicon obtained in step B is compared with the reference sequence. Nucleotide differences between the sequence information of each member in the family and the reference sequence are determined. A difference lower than a predetermined value in the family is determined as an error in PCR or sequencing, and a difference higher than the predetermined value is determined as a mutation. For example, in a family, when 99% of members have 15G>C, 1% of members 26C>T and 0.5% of members 36C>G, 15G>C is a true mutation, and 26C>T and 36C>G are determined to be errors. This family is determined to be generated from a polynucleotide molecule having a 15G>C mutation. This treatment is performed in all families, and it is determined whether each family is a mutant or wild type.

In step D', the ratio of mutant families to the total number of families is calculated. This ratio is compared with a predetermined threshold value, and when it is higher than the threshold value, the target nucleic acid is determined to be a mutant, and when it is lower than the threshold value, the target nucleic acid is determined to be a wild type. For example, when 70000 families of mutant families are detected, 30000 families of wild type families are detected, and the predetermined threshold is 30%, the target nucleic acid is determined to be a mutant.

2. Primer, Primer Set and Uses Thereof

The present disclosure includes a primer, a primer set and uses thereof. The primer in one embodiment is the tagged primer described in the above 1., the description of the above 1. being incorporated herein. The primer set contains the forward and reverse primers described in the above 1., the description of the above 1. being incorporated herein. These uses are the use of the primer or primer set described above for the method of determining a target nucleic acid sequence, and the description of the above 1. is incorporated herein.

3. Target Nucleic Acid Sequencing Apparatus

[3-1. Target Nucleic Acid Sequencing Apparatus]
[3-1-1. Hardware Configuration]

A target nucleic acid analysis apparatus 10 includes at least a processing unit 101 and a storage unit. The storage unit is configured by a main storage unit 102 and/or an auxiliary storage unit 104. The target nucleic acid analysis apparatus 10 may be an apparatus for realizing the method stated in the claims or the above 1. In the explanation of the target nucleic acid analysis apparatus 10 and the operation of the target nucleic acid analysis apparatus 10, the description of the above 1 is incorporated herein for terms common to the terms described in the above 1.

The processing unit 101 determines the sequence of the target region.

Figure 9A:
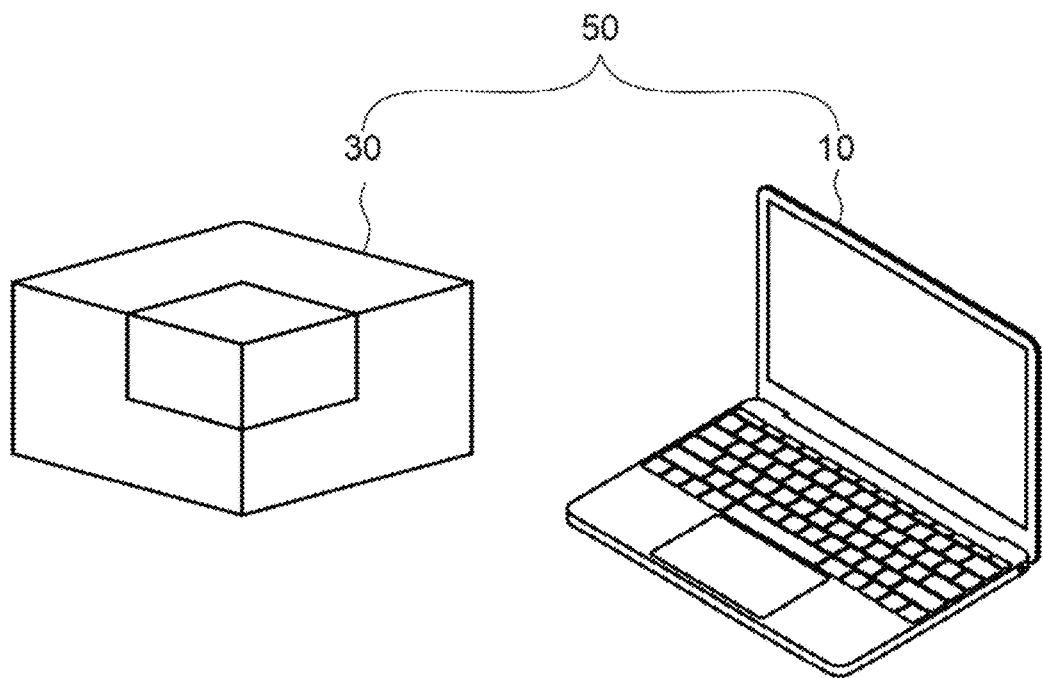
FIGS. 9A-9B show diagrams of configurations of a target nucleic acid sequencing apparatus.
Figure 9B:
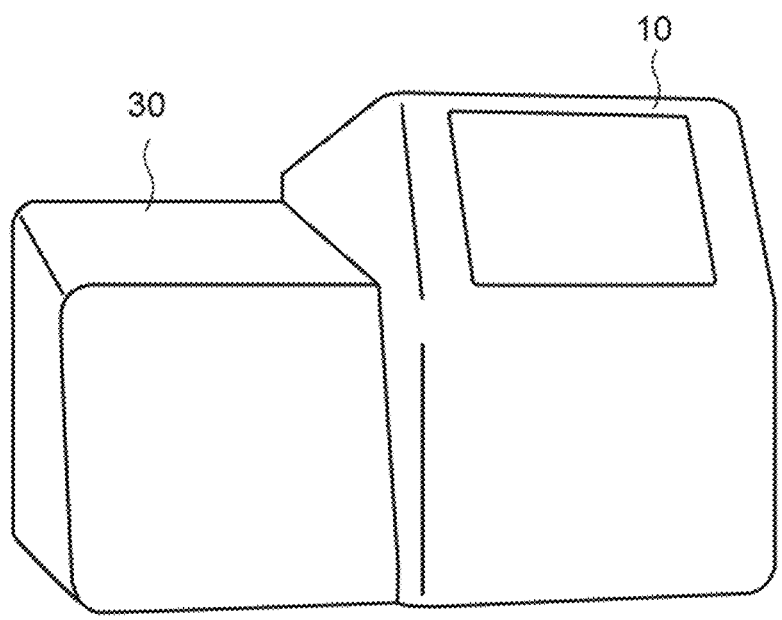
Figure 10:
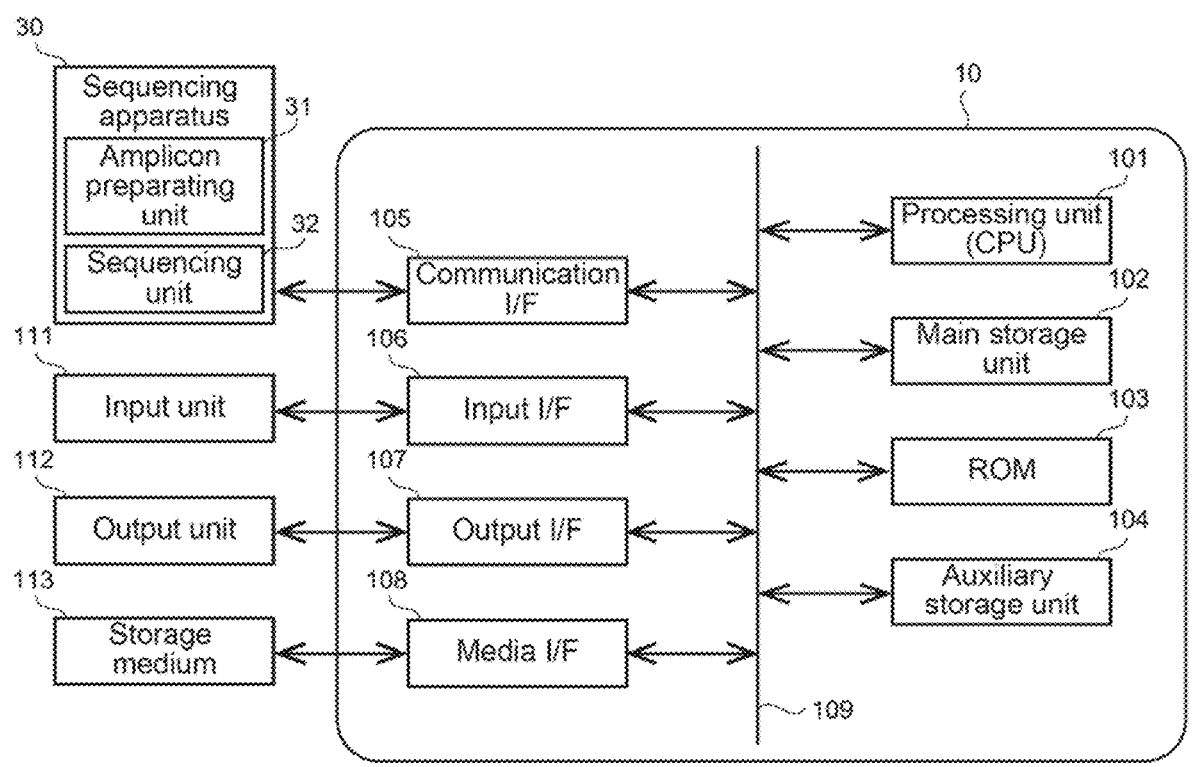
FIG. 10 is a diagram showing an outline of a hardware configuration of a target nucleic acid sequencing apparatus.

FIG. 9 and FIG. 10 show the configuration of the target nucleic acid analysis apparatus 10. The target nucleic acid analysis apparatus 10 may be connected to an input unit 111, an output unit 112, and a storage medium 113. The target nucleic acid analysis apparatus 10 may be connected to a sequencing apparatus 30 that performs sequencing. The target nucleic acid analysis apparatus 10 may constitute a target nucleic acid sequence sequencing system 50 connected to the sequencing apparatus 30 directly or via a network or the like (FIG. 9A). The target nucleic acid analysis apparatus 10 and the sequencing apparatus 30 may be integrated as shown in FIG. 9B.

As shown in Table 10, in the target nucleic acid analysis apparatus 10, a processing unit 101, a main storage unit 102, a ROM (read only memory) 103, an auxiliary storage unit 104, a communication interface (I/F) 105, an input interface (I/F) 106, an output interface (I/F) 107 and a media interface (I/F) 108 are data-communicably connected with each other via a bus 109.

The processing unit 101 is configured by a CPU, an MPU, a GPU, or the like. The processing unit 101 executes a computer program stored in the auxiliary storage unit 104 or the ROM 103 and processes data to be obtained so that the target nucleic acid analysis apparatus 10 functions.

The ROM 103 is configured by a mask ROM, a PROM, an EPROM, an EEPROM and the like, and a computer program executed by the processing unit 101 and data used for the computer program are recorded in the ROM 103. When starting the target nucleic acid analysis apparatus 10, the ROM 103 stores a boot program executed by the processing unit 101 and programs and settings related to the operation of hardware of the target nucleic acid analysis apparatus 10.

The main storage unit 102 is configured by a RAM (Random Access Memory) such as SRAM or DRAM. The main storage unit 102 is used for reading the computer program recorded in the ROM 103 and the auxiliary storage unit 104. The main storage unit 102 is used as a work area when the processing unit 101 executes these computer programs.

The auxiliary storage unit 104 is configured by a semiconductor memory element such as a hard disk and a flash memory, an optical disk, and the like. In the auxiliary storage unit 104, various computer programs to be executed by the processing unit 101, such as operating systems and application programs, and various setting data used for executing computer programs are stored. The auxiliary storage unit 104 stores the sequences of the tagged primer and each section constituting the tagged primer, the length of the sequences of the tagged primer and each section constituting the tagged primer, the predetermined value of the consensus rate, and the like. The auxiliary storage unit 104 may store the sequence information obtained from the sequencing apparatus 30. The auxiliary storage unit 104 may store reference sequences and the like obtained via the network.

The communication I/F 105 is configured by serial interfaces such as USB, IEEE1394 and RS-232C, parallel interfaces such as SCSI, IDE and IEEE1284, an analog interface including a D/A converter and an A/D converter, a network interface controller (Network interface controller: NIC), and the like. Under the control of the processing unit 101, the communication I/F 105 receives the data from the sequencing apparatus 30 or another external device, and the communication I/F 105 transmits or displays information stored in or generated by the target nucleic acid analysis apparatus 10 as necessary to the sequencing apparatus 30 or to the outside. The communication I/F 105 may communicate with the sequencing apparatus 30 or another external device (not shown, for example, another computer, or a cloud system) via a network.

The input I/F 106 is configured by, for example, serial interfaces such as USB, IEEE1394 and RS-232C, parallel interfaces such as SCSI, IDE and IEEE1284, an analog interface including a D/A converter an A/D converter, and the like. The input I/F 106 receives character input, click, voice input and the like from the input unit 111. The received input content is stored in the main storage unit 102 or the auxiliary storage unit 104.

The input unit 111 is configured by a touch panel, a keyboard, a mouse, a pen tablet, a microphone, and the like. The input unit 111 performs character input or voice input to the target nucleic acid analysis apparatus 10. The input unit 111 may be connected from outside the target nucleic acid sequencing apparatus 10 or integrated with the target nucleic acid analysis apparatus 10.

The output I/F 107 is configured by, for example, the same interface as the input I/F 106. The output I/F 107 outputs the information generated by the processing unit 101 to the output unit 112. The output I/F 107 outputs the information generated by the processing unit 101 and stored in the auxiliary storage unit 104, to the output unit 112.

The output unit 112 is configured by, for example, a display, a printer, and the like. The output unit 112 displays the measurement results transmitted from the sequencing apparatus 30, various operation windows in the target nucleic acid analysis apparatus 10, analysis results, and the like.

The media I/F 108 reads, for example, application software or the like stored in the storage medium 113. The read application software or the like is stored in the main storage unit 102 or the auxiliary storage unit 104. The media I/F 108 writes the information generated by the processing unit 101 in the storage medium 113. The media I/F 108 writes the information generated by the processing unit 101 and stored in the auxiliary storage unit 104 to the storage medium 113.

The storage medium 113 is configured by a flexible disk, CD-ROM, DVD-ROM, or the like. The storage medium 113 is connected to the media I/F 108 by a flexible disk drive, a CD-ROM drive, a DVD-ROM drive, or the like. In the storage medium 113, an application program or the like for allowing the computer to execute operation may be stored.

The processing unit 101 may obtain application software and various settings necessary for controlling the target nucleic acid analysis apparatus 10 via a network, instead of reading from the ROM 103 or the auxiliary storage unit 104. The application program is stored in the auxiliary storage unit of the server computer on the network, and it is also possible that the target nucleic acid analysis apparatus 10 accesses the server computer to download the computer program and store it in the ROM 103 or the auxiliary storage unit 104.

In the ROM 103 or the auxiliary storage unit 104, an operation system for providing a graphical user interface environment such as Windows (registered trademark) manufactured and sold by Microsoft Corporation is installed. The computer program to be described later is assumed to operate on the operating system. That is, the target nucleic acid analysis apparatus 10 may be a general-purpose computer such as a personal computer.

[3-1-2. Configuration of Sequencing Apparatus]

The sequencing apparatus 30 is not limited as long as it can analyze a nucleotide sequence. As shown in FIG. 10, the sequencing apparatus 30 may further include an amplicon preparing unit 31 in addition to a sequencing unit 32. The sequencing apparatus 30 is preferably a next generation sequencer. Examples of the next generation sequencer include the device described in the above 1-2-2.

[3-1-3. Operation of Target Nucleic Acid Sequencing Apparatus]

An example of the operation of the target nucleic acid analysis apparatus 10 will be described with reference to FIG. 11. The following operations are processed by the processing unit 101 according to a computer program to be described later.

The processing unit 101 obtains sequence information obtained by the sequencing apparatus 30, for example, in accordance with an instruction to start processing inputted from the input unit 111 by the user (Step S20). At this time, for example, when reading sequence information by input from the input unit 111 by the user, or from the sequencing apparatus 30, the processing unit 101 obtains an identification number (subject ID) for identifying a subject from whom a sample was obtained, a sample identification ID for identifying the type (blood, tissue, formalin fixed/paraffin embedded (FFPE) tissue) of sample, an identification number (target nucleic acid identification ID) for identifying a target nucleic acid, an identification number (target region identification ID) for identifying a target nucleic acid, and the like. The obtained sequence information, identification ID and the like are stored in the main storage unit 102 and/or the auxiliary storage unit 104.

Figure 11:
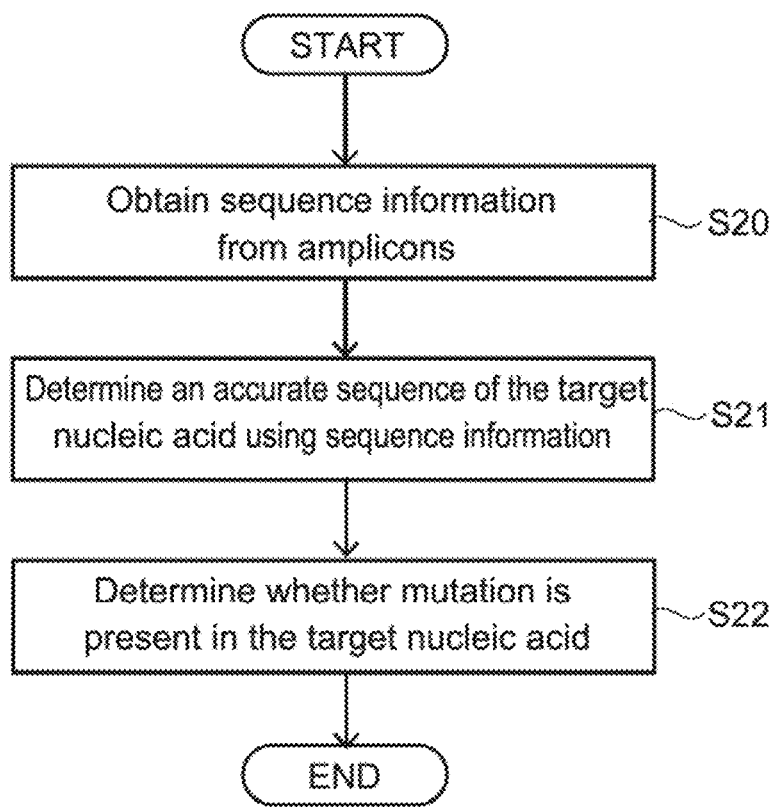
FIG. 11 is a flowchart showing an example of processing of the target nucleic acid sequencing apparatus.
Figure 12:
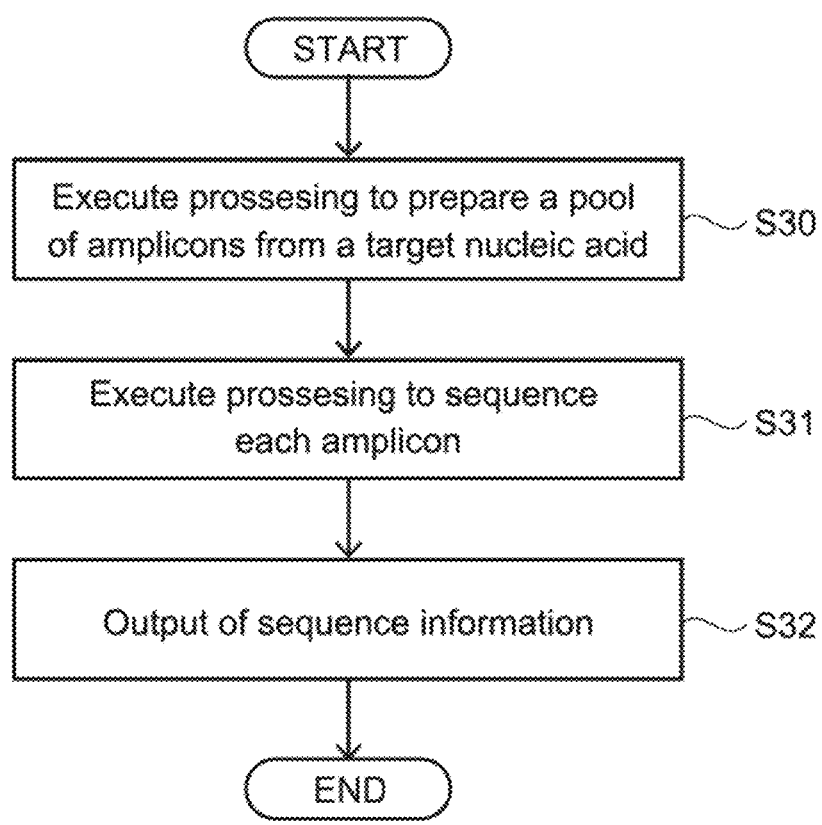
FIG. 12 is a flowchart showing an example of processing of the sequencing apparatus.

The processing unit 101 may make the amplicon preparing unit 31 execute processing to prepare amplicons from a target nucleic acid (Step S30) shown in FIG. 12, before Step S20 shown in FIG. 11. Further, the processing unit 101 may make the sequencing unit 32 execute a processing for sequencing each amplicon amplified in Step S30 (Step S31). In this case, the target nucleic acid is set in the sequencing apparatus 30 by the user. In accordance with an instruction to start processing inputted from the input unit 111 by the user, the processing unit starts Step S30. Step S31 may be started in accordance with a user's instruction to start processing or may be continued after the end of Step S30.

Next, the processing unit 101 outputs the sequence information obtained by sequencing to the target nucleic acid analysis apparatus 10 (Step S32).

For the same terms as the terms used in the above 1-3., the description is incorporated into the description of this section.

[3-3. Other Processing]

Figure 13:
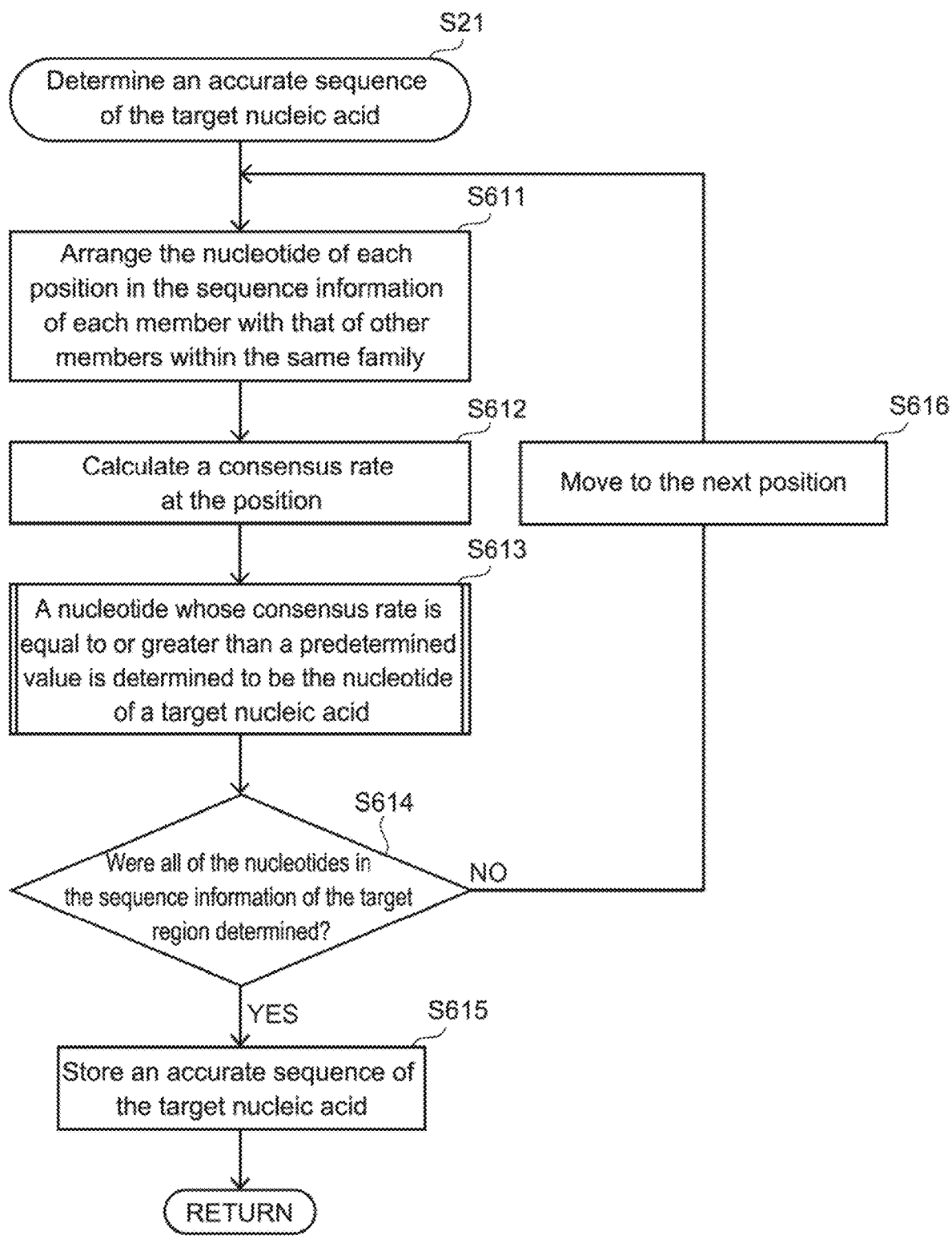
FIG. 13 is a flowchart showing a method for determining the sequence of a target region.

Further, the processing unit 101 may perform the processing of determining the accurate sequence of the target region shown in FIG. 13 in Step S21 of FIG. 11. In Step S22 of FIG. 11, the processing unit 101 may perform determination processing as to whether or not there is a mutation in the target sequence shown in FIG. 14.

An example of a processing for determining the accurate sequence of the target region will be specifically described, with reference to FIG. 13. The processing unit 101 performs the processing for determining the accurate sequence of the target region in Step S21 of FIG. 11. In this processing, the processing unit 101 first aligns a nucleotide of each position in the sequence information of each member with the same position of other members for each member within the family having the same UID sequence (Step S611).

Next, the processing unit 101 calculates the consensus rate of the position (Step S612).

The processing unit 101 compares the consensus rate calculated in Step S612 with the predetermined value of the consensus rate stored in the auxiliary storage unit 104, and the processing unit 101 determines a nucleotide whose consensus rate is equal to or larger than the predetermined value as the nucleotide of the target region (Step S613).

The processing unit 101 determines whether nucleotides have been determined for all positions in the target region. When nucleotides have not been determined for all positions in the target region, the processing unit 101 returns to Step S611 and repeats Steps S611 to S614 until nucleotides are determined for all positions in the target region.

When nucleotides have been determined for all positions in the target region, the processing unit 101 proceeds to Step S615, and an accurate sequence of the target region is stored in the auxiliary storage unit 104, or the like.

The processing unit 101 may output the accurate sequence of the target region to the output unit 112.

Figure 14:
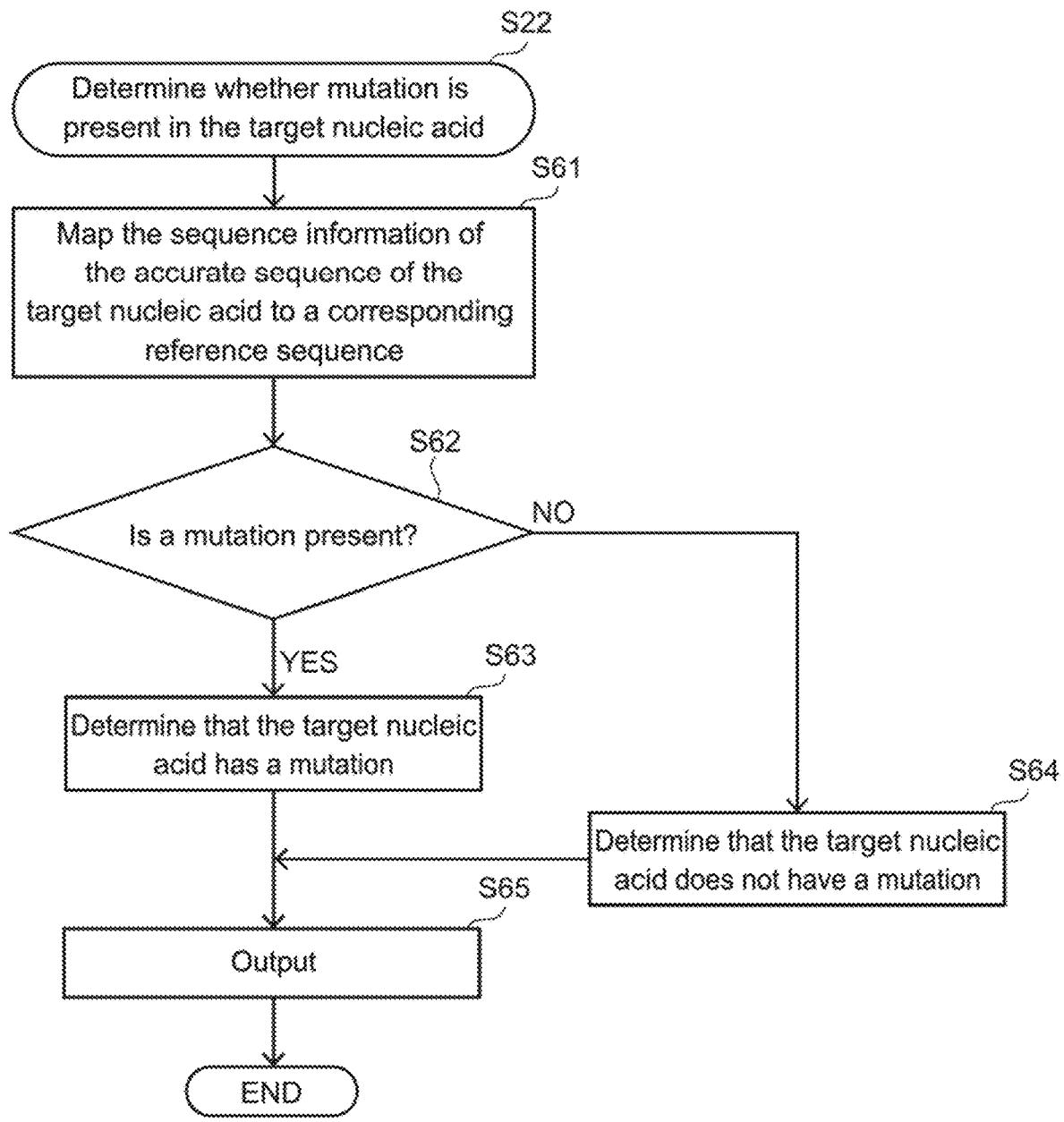
FIG. 14 is a flowchart showing accurate processing.

An example of a processing for determining whether or not there is a mutation in the accurate sequence of the target region will be specifically described, with reference to FIG. 14. The processing unit 101 maps the sequence information of the accurate sequence of the target region determined in Step S21 of FIG. 11 to a reference sequence corresponding to the sequence information (Step S61). The reference sequence is as described in the above 1-4. The reference sequence may be stored in the auxiliary storage unit 104, or may be obtained at the time of determining the sequence via a network. Mapping may be performed by sending the sequence information to a server or the like in which the reference sequence is stored via the network.

The processing unit 101 compares the sequence information with the reference sequence (including a mutated sequence registered in the mutation information database) by mapping.

The processing unit 101 determines whether or not there is a mutated sequence in the sequence information (Step S62).

When there is no mutated sequence in the sequence information, the processing unit 101 determines that the target region has no mutation (Step S63). When the mutated sequence is not an accurate mutation (NO), it is determined that there is no mutation in the target region (Step S64).

The processing unit 101 may store the determination results of the sequence of the target region in the auxiliary storage unit 104 or may output them to the output unit 112 (Step S65). As described in the above 1-4., the output destination can be a monitor of a sequencing apparatus, another terminal, a printer, or the like.

4. Computer Program

The computer program is a program for controlling the target nucleic acid analysis apparatus 10 and the target nucleic acid sequence determining system 50, in the method for sequencing a target nucleic acid as described in the above 1.

The computer program controls the target nucleic acid analysis apparatus 10 and the target nucleic acid sequence determination system 50 by making the processing unit 101 execute Steps S20 to S21; Steps S30, S31, and Steps S20 to S21; Steps S20 to S22, Steps S60 to S65, and Steps S611 to S615; Steps S30, S31, Steps S20 to S22, Steps S60 to S65, and Steps S611 to S615, described in the above 3-1-2. and 3-3.

The computer program may be stored in a storage medium. That is, the computer program is stored in a semiconductor memory element such as a hard disk or a flash memory, or a storage medium such as an optical disk. The computer program may be stored in a storage medium connectable via a network such as a cloud server. The computer program may be in a download form or a program product stored in the storage medium.

The storage format of the program in the storage medium is not limited as long as the presented apparatus can read the program. Storage into the storage medium is preferably nonvolatile.

5. Examples

Sequences of forward primers (tagged primers) and a sequence of reverse primer used in this analysis are shown in Table 1. In splitUID1 to splitUID9, predetermined nucleotides are inserted in UID. In the forward primers of Table 1, CCTACACGACGCTCTTCCGATCT (SEQ ID NO: 7) located on 5' side is a region to which a universal primer binds, and also functions as a binding region of a sequencing primer. TCTTAAAAGGTCTTTGATTTGCG (SEQ ID NO: 8) located on 3' side is a region that hybridizes to a target nucleic acid SMAD4 gene. In the reverse primer of Table 1, TCAGACGTGTGCTCTTCCGATCT (SEQ ID NO: 9) located on 5' side is a region to which a universal primer binds. TGCAGTAGCCGCCTGC (SEQ ID NO: 10) located on 3' side is a region that hybridizes to the target nucleic acid SMAD4 gene.

Sequence analysis was performed for the SMAD4 gene using next generation sequencer MiSeq (registered trademark) of Illumina Inc.

TABLE 1

| Name | Sequence | SEQ ID NO: |
|---|---|---|
| iPSS0301_FWD_normal UID | CCTACACGACGCTCTTCCGA TCTNNNNNNNNNNNNNNNTCT TAAAAGGTCTTTGATTTGCG | 11 |
| iPSS0802_FWD_splitUID1 | CCTACACGACGCTCTTCCGA TCTNNNNNNNNTTTTTTTNNN NNNNTCTTAAAAGGTCTTTG ATTTGCG | 12 |
| iPSS0808_FWD_splitUID2 | CCTACACGACGCTCTTCCGA TCTNNNNNNNNTNTNTNTNTN TNTNTCTTAAAAGGTCTTTG ATTTGCG | 13 |
| iPSS0946_FWD_splitUID3 | CCTACACGACGCTCTTCCGA TCTTNNTNNTNNTNNTNNTN NTNNTCTTAAAAGGTCTTTG ATTTGCG | 14 |
| iPSS0947_FWD_splitUID4 | CCTACACGACGCTCTTCCGA TCTNNNNNNNNAAAAAAAANNN NNNNTCTTAAAAGGTCTTTG ATTTGCG | 15 |
| iPSS0948_FWD_splitUID5 | CCTACACGACGCTCTTCCGA TCTNNNNNNNNCCCCCCCNNN NNNNTCTTAAAAGGTCTTTG ATTTGCG | 16 |
| iPSS0949_FWD_splitUID6 | CCTACACGACGCTCTTCCGA TCTNNNNNNNGGGGGGGNNN NNNNTCTTAAAAGGTCTTTG ATTTGCG | 17 |
| iPSS0950_FWD_splitUID7 | CCTACACGACGCTCTTCCGA TCTNNNNNNNNATCGATCNNN NNNNTCTTAAAAGGTCTTTG ATTTGCG | 18 |
| iPSS0951_FWD_splitUID8 | CCTACACGACGCTCTTCCGA TCTNNNNNNNNTTTTTNNNNNN NNTCTTAAAAGGTCTTTGAT TTGCG | 19 |
| iPSS0952_FWD_splitUID9 | CCTACACGACGCTCTTCCGA TCTNNNNNNNNTTTNNNNNNN TCTTAAAAGGTCTTTGATTT GCG | 20 |
| iPSS0953_FWD_splitUID10 | CCTACACGACGCTCTTCCGA TCTNNNNNNNNTNNNNNNNTC TTAAAAGGTCTTTGATTTGC G | 21 |
| iPSS0956_FWD_splitUID13 | CCTACACGACGCTCTTCCGA TCTNNNNNNNNANANANANAN ANANTCTTAAAAGGTCTTTG ATTTGCG | 22 |
| iPSS0957_FWD_splitUID14 | CCTACACGACGCTCTTCCGA TCTNNNNNNNNCNCNCNCNCN CNCNTCTTAAAAGGTCTTTG ATTTGCG | 23 |

TABLE 1-continued

| Name | Sequence | SEQ ID NO: |
|---|---|---|
| iPSS0958_FWD_splitUID15 | CCTACACGACGCTCTTCCGATCTNNNNNNNNGNGNGNGNGNGNGNTCTTAAAAGGTCTTTGATTTGCG | 24 |
| iPSS0302_REV | TCAGACGTGTGCTCTTCCGATCTTGCAGTAGCCGCCTGC | 25 |

Figure 15:
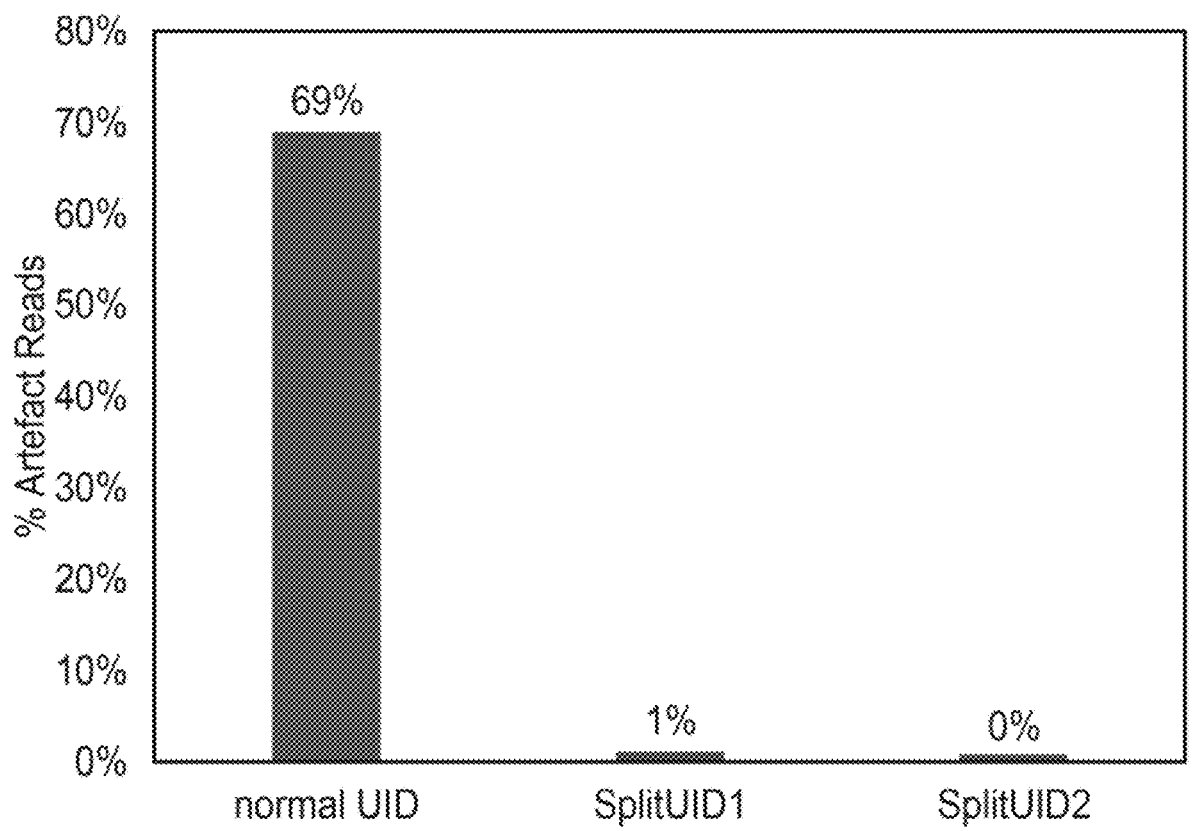
FIG. 15 shows a percentage of artefact reads when performing NGS analysis for an amplicon of SMAD4 subjected to UID-PCR using each of a tagged primer having normal UID sequence as UID, a tagged primer having splitUID1 sequence as UID, and a tagged primer having splitUID2 sequence as UID.

FIG. 15 shows a percentage of artefact reads when analyzed by NGS using tagged primers with different UID sequences. Here, the artefact read refers to a read containing a sequence different from that of the target region, and is considered to be derived from a by-product nonspecifically produced by PCR. Using a primer having normal UID sequence as UID, a primer having splitUID1 sequence as UID or a primer having splitUID2 sequence as UID as the forward primer, UID-PCR was performed with the reverse primer. Using this amplicon as a template, WBC-PCR was performed using a universal primer to obtain an amplification product. The obtained amplification product was purified once with DNA purification reagent AMPure XP and subjected to NGS. When the normal UID was used, the artefact read was contained nearly 70%. On the other hand, in splitUID1 in which a predetermined nucleotide was inserted into UID, the artefact read was 1% or less, and no artefact read was detected in splitUID2.

Figure 16:
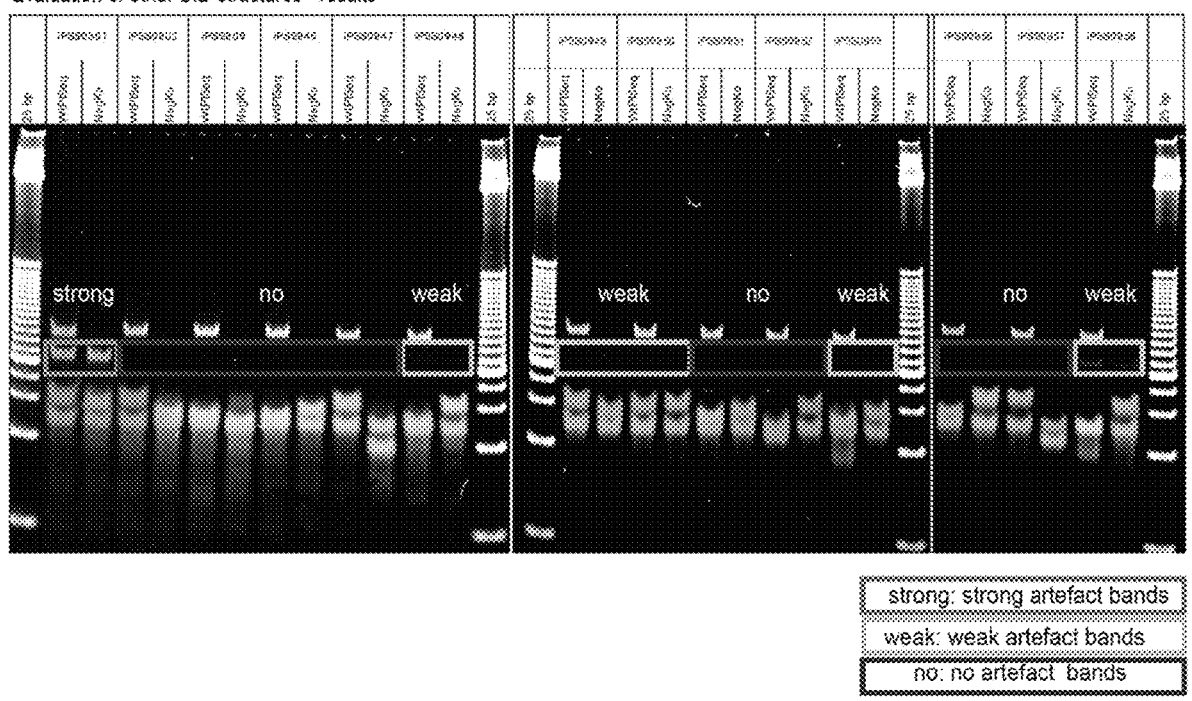
FIG. 16 shows results of performing UID-PCR using each of tagged primers and reverse primer shown in Table 1, performing WBC-PCR on the product using universal primers, and electrophoresing PCR products.

FIG. 16 shows results of electrophoresing PCR products obtained by performing UID-PCR using each tagged primer and reverse primer shown in Table 1 and performing WBC-PCR on the amplicon using universal primers. WtPISeq indicates a lane amplified by adding template DNA, and NegKo indicates a lane amplified without adding template DNA. A band detected by NegKo is an artefact band. In iPSS0301 (normal UID), a strong band indicating a nonspecific amplification product was detected in a part indicated by a rectangular box. On the other hand, no artefact band was detected in iPSS0802 (splitUID1), iPSS0808 (splitUID2), iPSS0946 (splitUID3), iPSS0947 (splitUID4), iPSS0951 (splitUID8), iPSS0952 (splitUID9), iPSS0956 (splitUID13), and iPSS0957 (splitUID14). Although artefact bands were detected in iPSS0948 (splitUID5), iPSS0949 (splitUID6), iPSS0950 (splitUID7), iPSS0953 (splitUID10), and iPSS0958 (splitUID15), they were extremely weak bands compared to that in iPSS0301 (normal UID).

From the above results, it was shown that incorporation of predetermined nucleotides other than random nucleotides in UID is useful for suppressing generation of nonspecific amplification products.

As a comparison, Stahlberg et al., Simple, multiplexed, PCR-based barcoding of DNA enables sensitive mutation detection in liquid biopsies using sequencing, Nucleic Acids Research, Volume 44, Issue 11, 20 Jun. 2016, Page e105 shows the hairpin barcode primer described in US 2018/051,277 A1 produces artefacts (see FIG. 3B; there are some peaks around 130-200 bp which should be non-specific products).

The invention claimed is:

1. A method for sequencing a nucleotide sequence of a target nucleic acid, comprising:
   providing a pool of amplicons, wherein the pool of amplicons is prepared by a process comprising PCR amplification of a target nucleic acid using primers each containing a unique identifier; and
   sequencing the amplicons comprising the unique identifier and the target nucleic acid,
   wherein the nucleotide sequence of the unique identifier contains a plurality of random nucleotides (N) and a plurality of predetermined nucleotides,
   wherein a nucleotide at the 5' end of the unique identifier is a random nucleotide (N), and a nucleotide at the 3' end of the unique identifier is a random nucleotide (N), and
   wherein all of said predetermined nucleotides are each independently selected from the group consisting of nucleotides comprising adenine as a base, and nucleotides comprising thymine as a base.

2. The method according to claim 1, wherein 6% to 90% of the nucleotides of the unique identifier are predetermined nucleotides.

3. The method according to claim 1, wherein the nucleotide number of the unique identifier is Z nt, and the unique identifier comprises 1 nt to Z/2 nt of predetermined nucleotides.

4. The method according to claim 1, wherein the length of the unique identifier is 4 nt or more.

5. The method according to claim 1, wherein the length of the unique identifier is 100 nt or less.

6. A method for sequencing a nucleotide sequence of a target nucleic acid, comprising:
   providing a pool of amplicons, wherein the pool of amplicons is prepared by amplifying the target nucleic acid using tagged primers each containing: (i) a universal primer section; and (ii) a tag section containing a unique identifier to produce tagged target nucleic acids, and amplifying the tagged target nucleic acids using universal primers to produce the pool of amplicons; and
   sequencing the amplicons comprising the unique identifier and the target nucleic acid,
   wherein the nucleotide sequence of the unique identifier contains a plurality of random nucleotides (N) and a plurality of predetermined nucleotides,
   wherein a nucleotide at the 5' end of the unique identifier is a random nucleotide (N), and a nucleotide at the 3' end of the unique identifier is a random nucleotide (N), and
   wherein all of said predetermined nucleotides are each independently selected from the group consisting of nucleotides comprising adenine as a base, and nucleotides comprising thymine as a base.

7. The method according to claim 1, wherein said plurality of predetermined nucleotides includes a plurality of nucleotides comprising adenine as a base.

8. The method according to claim 6, wherein said plurality of predetermined nucleotides contains a plurality of nucleotides comprising adenine as a base.

9. The method according to claim 1, wherein said plurality of predetermined nucleotides contains a plurality of nucleotides comprising thymine as a base.

10. The method according to claim 6, wherein said plurality of predetermined nucleotides contains a plurality of nucleotides comprising thymine as a base.

11. The method according to claim 1, wherein the nucleotide sequence of the unique identifier is one or more nucleotide sequence of the unique identifier contained in SEQ ID NOs: 12-15 and 19-22.

12. The method according to claim 6, wherein the nucleotide sequence of the unique identifier is one or more nucleotide sequence of the unique identifier contained in SEQ ID NOs: 12-15 and 19-22.

* * * * *